(12) United States Patent  (10) Patent No.: US 8,231,983 B2
Sugita et al.  (45) Date of Patent: Jul. 31, 2012

(54) ORGANIC ELECTROLUMINESCENT DEVICE, DISPLAY AND ILLUMINATING DEVICE

(75) Inventors: Shuichi Sugita, Akishima (JP); Tatsuo Tanaka, Sagamihara (JP)

(73) Assignee: Konica Minolta Holdings Inc. (JP)

( * ) Notice: Subject to any disclaimer, the term of this patent is extended or adjusted under 35 U.S.C. 154(b) by 787 days.

(21) Appl. No.: 11/911,425

(22) PCT Filed: Mar. 27, 2006

(86) PCT No.: PCT/JP2006/306079
§ 371 (c)(1),
(2), (4) Date: Oct. 12, 2007

(87) PCT Pub. No.: WO2006/114966
PCT Pub. Date: Nov. 2, 2006

(65) Prior Publication Data
US 2009/0066226 A1  Mar. 12, 2009

(30) Foreign Application Priority Data
Apr. 18, 2005 (JP) ................................ 2005-119503

(51) Int. Cl.
*H01L 51/54* (2006.01)

(52) U.S. Cl. ..... 428/690; 428/917; 257/40; 257/E51.05; 546/79; 528/394; 528/397; 528/422

(58) Field of Classification Search .................. 428/690, 428/917; 313/504, 505, 506; 257/40, E51.05; 546/79; 528/394, 397, 422
See application file for complete search history.

(56) References Cited

U.S. PATENT DOCUMENTS

| 6,097,147 A | 8/2000 | Baldo et al. | |
| 2003/0168970 A1* | 9/2003 | Tominaga et al. | 313/504 |
| 2005/0031899 A1* | 2/2005 | Nomura et al. | 428/690 |
| 2005/0069729 A1* | 3/2005 | Ueda et al. | 428/690 |
| 2005/0175858 A1* | 8/2005 | Jung et al. | 428/690 |

FOREIGN PATENT DOCUMENTS

| JP | 63-264692 A | | 11/1988 |
| JP | 3-255190 A | | 11/1991 |
| JP | 5-109485 A | | 4/1993 |
| JP | 06-056777 | * | 3/1994 |

(Continued)

OTHER PUBLICATIONS

English Translation of JP 2004-300044.*

(Continued)

*Primary Examiner* — Jennifer Chriss
*Assistant Examiner* — Gregory Clark
(74) *Attorney, Agent, or Firm* — Cantor Colburn LLP

(57) ABSTRACT

Disclosed is an organic electroluminescent device having high emission luminance, high external quantum efficiency and long lifetime. Also disclosed are a display and an illuminating device. The organic electroluminescent device is characterized in that it comprises, between a pair of electrodes, a constituent layer including at least a phosphorescence emission layer, wherein at least one in the constituent layer contains a compound represented by formula (1),

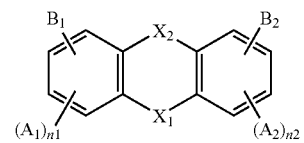

Formula (1)

16 Claims, 3 Drawing Sheets

FOREIGN PATENT DOCUMENTS

| | | |
|---|---:|---|
| JP | 7-53950 A | 2/1995 |
| JP | 10-226785 A | 8/1998 |
| JP | 2000-30275 A | 1/2000 |
| JP | 3-093796 B2 | 10/2000 |
| JP | 2001-43979 A | 2/2001 |
| JP | 2003-261471 A | 9/2003 |
| JP | 2004-300044 * | 10/2004 |
| WO | WO2006114966 A1 | 11/2006 |

OTHER PUBLICATIONS

Lim et. al., Intermolecular Triplet excimers . . . Dibenzofuran and Dibenzothiophene, 1992, J. of Phys. Chem. vol. 96, No. 7, p. 2935-2937.*

Uekawa et. al., . . . Carbazole groups in electroluminscent devices, 1999,Thin Solid Films, vol. 352, pp. 185-188.*

English Translation of JP 07-053950 (translated Jul. 27, 2010).*

* cited by examiner

ORGANIC ELECTROLUMINESCENT DEVICE, DISPLAY AND ILLUMINATING DEVICE

FIELD OF THE INVENTION

This invention relates to an organic electroluminescent device, a display and an illuminating device.

TECHNICAL BACKGROUND

As an emission type electronic displaying device, there is an electroluminescent device (ELD). As devices constituting the ELD, there are mentioned an inorganic electroluminescent device and an organic electroluminescent device (hereinafter also referred to as organic EL device). The inorganic electroluminescent device has been used for a plane-shaped light source, but a high voltage alternating current has been required to drive the device.

An organic EL device has a structure in which a light emission layer containing a light emission compound is arranged between a cathode and an anode, and an electron and a hole were injected into the light emission layer and recombined to form an exciton. The device emits light, utilizing light (fluorescent light or phosphorescent light) generated by inactivation of the exciton, and the device can emit light by applying a relatively low voltage of from several volts to several decade volts. The device has a wide viewing angle and a high visuality since the device is of self light emission type. Further, the device is a thin, complete solid device, and therefore, the device is noted from the viewpoint of space saving and portability.

An organic EL device for practical use is required which efficiently emits light with high luminance at a lower power. For example, there are disclosed a device with long lifetime emitting light with high luminance in which stilbene derivatives, distyrylarylene derivatives or tristyrylarylene derivatives are doped with a slight amount of a fluorescent compound (Patent document 1 below), a device which comprises an organic light emission layer containing an 8-hydroxyquinoline aluminum complex as a host compound doped with a slight amount of a fluorescent compound (Patent document 2 below), and a device which comprises an organic light emission layer containing an 8-hydroxyquinoline aluminum complex as a host compound doped with a quinacridone type dye (Patent document 3 below).

When light emitted through excited singlet state is used in the device disclosed in the above Patent documents, the upper limit of the external quantum efficiency ($\eta$ext) is considered to be at most 5%, as the generation ratio of singlet excited species to triplet excited species is 1:3, that is, the generation probability of excited species capable of emitting light is 25%, and further, external light emission efficiency is 20%.

Since an organic EL device, employing phosphorescence through the excited triplet, was reported by Prinston University (for example, see non-patent document 1 below), study on materials emitting phosphorescence at room temperature has been actively made (for example, see Non-patent document 2 or Patent document 4 below). As the upper limit of the internal quantum efficiency of the excited triplet is 100%, the light emission efficiency of the exited triplet is theoretically four times that of the excited singlet. Accordingly, light emission employing the excited triplet exhibits the same performance as a cold cathode tube, and can be applied to illumination. For example, many kinds of heavy metal complexes such as iridium complexes has been synthesized and studied (for example, see Non-patent document 3 below).

An example employing tris(2-phenylpyridine)iridium as a dopant has been studied (for example, see Non-patent document 2 below). Further, an example employing as a dopant $L_2$Ir (acac) (in which L represents a bidentate ligand, and "acac represents acetyl acetone) such as (ppy)$_2$Ir (acac) (for example, see Non-patent document 4 below), or employing as a dopant tris(2-p-tolylpyridine)iridium {Ir(ptpy)$_3$}, tris(benzo-[h]-quinoline)iridium {Ir(bzq)$_3$}, or Ir(bzq)$_2$ClP(Bu)$_3$ has been studied (for example, see Non-patent document 5 below).

A hole transporting material is used as a host of a phosphorescent compound in order to increase emission efficiency (for example, see Non-patent document 6 below).

Various kinds of electron transporting materials are used as a host of a phosphorescent compound, and further doped with a new iridium complex (for example, see Non-patent document 4 below). High emission efficiency is obtained by incorporation of a hole blocking layer (for example, see Non-patent document 5 below).

Also disclosed are compounds as thermally stable emission materials having a partial structure of a heterocyclic ring-containing polycyclic aromatic compound (see for example, Patent documents 5 and 6) and compounds as thermally stable hole transporting materials having a partial structure of a heterocyclic ring-containing polycyclic aromatic compound (see for example, Patent document 7). There is, however, no disclosure in these documents of a phosphorescence emission organic EL device.

Further disclosed are compounds having a fluorene joint (see for example, Patent document 8) as a thermally stable host materials), and compounds having a carbazole joint (see for example, Patent document 9). There is, however, no disclosure in these documents of a phosphorescence emission organic EL device.

A combination of a polycyclic aromatic compound and a phosphorescent compound is disclosed (see for example, Patent document 10), but it is not sufficient in view of emission efficiency or lifetime.

At present, an organic electroluminescent device emitting phosphorescence with further higher emission efficiency and longer lifetime has been studied. An external qauntum efficiency of around 20%, which is a theoretical threshold, is attained in green light emission, but in a low current region (a low luminance region), and the theoretical threshold is not attained in a high current region (a high luminance region). Further, a sufficient emission efficiency is not attained in another color emission, where there is room to be improved. An organic EL device for practical use is required which efficiently emits light with high luminance at a lower power. Particularly, an organic EL device is required which emits a blue phosphorescence with high efficiency.

Patent document 1: Japanese Patent No. 3093796
Patent document 2: Japanese Patent O.P.I. Publication No. 63-264692
Patent document 3: Japanese Patent O.P.I. Publication No. 3-255190
Patent document 4: U.S. Pat. No. 6,097,147
Patent document 5: Japanese Patent O.P.I. Publication No. 5-109485
Patent document 6: Japanese Patent O.P.I. Publication No. 7-53950
Patent document 7: Japanese Patent O.P.I. Publication No. 2001-43979
Patent document 8: Japanese Patent O.P.I. Publication No. 2000-30275
Patent document 9: Japanese Patent O.P.I. Publication No. 10-226785

Patent document 10: Japanese Patent O.P.I. Publication No. 2003-261471

Non-patent document 1: M. A. Baldo et al., Nature, 395, p. 151-154 (1998)

Non-patent document 2: M. A. Baldo et al., Nature, 403, 17, p. 750-753 (2000)

Non-patent document 3: S. Lamansky et al., J. Am. Chem. Soc., 123, 4304 (2001)).

Non-patent document 4: M. E. Tompson et. al., The 10$^{th}$ International Workshop on Inorganic and Organic Electroluminescence (EL' 00, Hamamatsu)

Non-patent document 5: Moon-Jae Youn. Og, Tetsuo Tsutsui et. al., The 10$^{th}$ International Workshop on Inorganic and Organic Electroluminescence (EL' 00, Hamamatsu).

Non-patent document 6: Ikai et. al., The 10$^{th}$ International Workshop on Inorganic and Organic Electroluminescence (EL' 00, Hamamatsu).

DISCLOSURE OF THE INVENTION

Problems to be Solved by the Invention

An object of the invention is to provide an organic electroluminescent device having high emission luminance, high external quantum efficiency and long lifetime, and an illuminating device and a display each employing the same.

Means for Solving the Above Problems

The above object of the invention can be attained by the following constitution:

(1) An organic electroluminescent device characterized in that it comprises, between a pair of electrodes, a constituent layer including at least a phosphorescence emission layer, wherein at least one in the constituent layer contains a compound represented by formula (1),

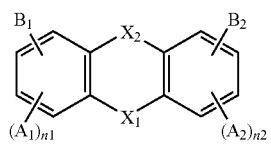

Formula (1)

wherein $A_1$ and $A_2$ represent a substituent; n1 and n2 independently represent an integer of from 0 to 3; $X_1$ represents an oxygen atom, a sulfur atom, an alkylene group, an imino group, a carbonyl group, a sulfoxide group or a sulfonyl group; $X_2$ represents an oxygen atom, a sulfur atom, an alkylene group, an imino group, a carbonyl group, a sulfoxide group, a sulfonyl group or a chemical bond; and $B_1$ and $B_2$ represent a group represented by formula (2),

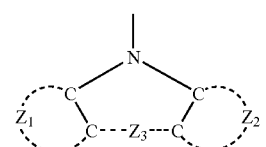

Formula (2)

wherein $Z_1$ and $Z_2$ represent an aromatic heterocyclic ring which may have a substituent, or an aromatic hydrocarbon ring; and $Z_3$ represents a divalent linkage group or a chemical bond.

(2) The organic electroluminescent device of item 1 characterized in that it comprises, between a pair of electrodes, a constituent layer including at least a phosphorescence emission layer, wherein at least one in the constituent layer contains a compound represented by formula (1),

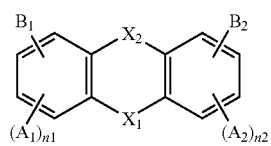

Formula (1)

wherein $A_1$ and $A_2$ represent a substituent; n1 and n2 independently represent an integer of from 0 to 3; $X_1$ and $X_2$ independently represent an oxygen atom, a sulfur atom, an alkylene group, an imino group, a carbonyl group, a sulfoxide group or a sulfonyl group; and $B_1$ and $B_2$ represent a group represented by formula (2),

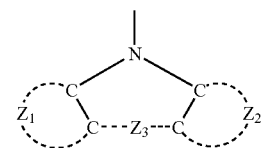

Formula (2)

wherein $Z_1$ and $Z_2$ represent an aromatic heterocyclic ring which may have a substituent, or an aromatic hydrocarbon ring; and $Z_3$ represents a divalent linkage group or a chemical bond.

(3) The organic electroluminescent device of item 1 characterized in that it comprises, between a pair of electrodes, a constituent layer including at least a phosphorescence emission layer, wherein at least one in the constituent layer contains a compound represented by formula (3),

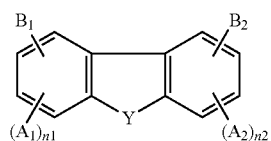

Formula (3)

wherein $A_1$ and $A_2$ represent a substituent; n1 and n2 independently represent an integer of from 0 to 3; Y represents an oxygen atom, a sulfur atom, an imino group, a sulfoxide group or a sulfonyl group; and $B_1$ and $B_2$ represent a group represented by formula (2),

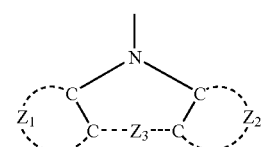

Formula (2)

wherein $Z_1$ and $Z_2$ represent an aromatic heterocyclic ring which may have a substituent, or an aromatic hydrocarbon ring; and $Z_3$ represents a divalent linkage group or a chemical bond.

(4) The organic electroluminescent device of item 1 characterized in that the compound represented by formula (3) is represented by formula (4),

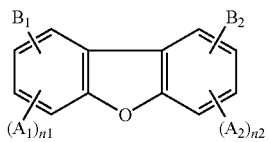

Formula (4)

wherein $A_1$ and $A_2$ represent a substituent; n1 and n2 independently represent an integer of from 0 to 3; and $B_1$ and $B_2$ represent a group represented by formula (2),

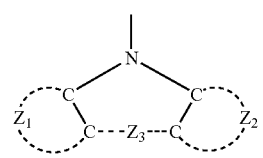

Formula (2)

wherein $Z_1$ and $Z_2$ represent an aromatic heterocyclic ring which may have a substituent, or an aromatic hydrocarbon ring; and $Z_3$ represents a divalent linkage group or a chemical bond.

(5) The organic electroluminescent device of item 1 characterized in that $Z_1$ of formula (2) represents an aromatic hydrocarbon ring.

(6) The organic electroluminescent device of item 1 characterized in that $Z_1$ of formula (2) represents an aromatic heterocyclic ring.

(7) The organic electroluminescent device of item 1 characterized in that the compound represented by formula (1) is contained in the phosphorescence emission layer.

(8) The organic electroluminescent device of item 1 characterized in that the constituent layer further includes at least one hole inhibiting layer containing the compound represented by formula (1).

(9) The organic electroluminescent device of item 1 characterized in that it emits a blue light.

(10) The organic electroluminescent device of item 1 characterized in that it emits a white light.

(11) A display characterized in that it comprises the organic electroluminescent device of item 1.

(12) An illuminating device characterized in that it comprises the organic electroluminescent device of item 1.

(13) A display characterized in that it comprises the illuminating device of item 12 and a liquid crystal device as a displaying means.

EFFECTS OF THE INVENTION

The present invention can provide an organic electroluminescent device having high emission luminance, high external quantum efficiency and long lifetime, and an illuminating device and a display each employing the same.

Figure 1:
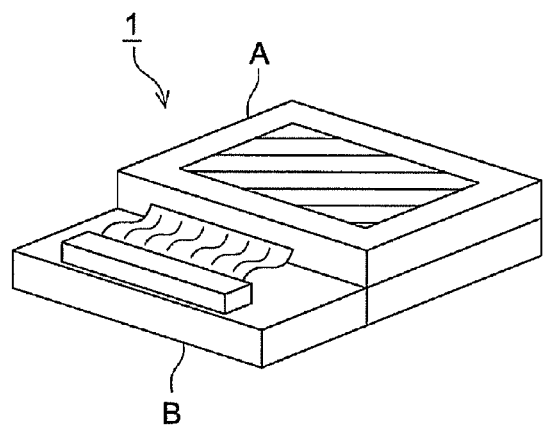
FIG. 1 shows a schematic drawing of one example of a display comprising an organic EL device.

| EXPLANATION OF SYMBOLS | |
|---|---|
| 1. | Display |
| 3. | Pixel |
| 5. | Scanning line |
| 6. | Data line |
| 7. | Electric source line |
| 10. | Organic EL device |
| 11. | Switching transistor |
| 12. | Driving transistor |
| 13. | Capacitor |
| A. | Display section |
| B. | Control section |
| 102. | Glass cover |
| 105. | Cathode |
| 106. | Organic EL layer |
| 107. | Glass substrate with transparent electrode |
| 108. | Nitrogen gas |
| 109. | Water trapping agent |

PREFERRED EMBODIMENT OF THE INVENTION

In the invention, the organic electroluminescent device is characterized in that it comprises, between a pair of electrodes, a constituent layer including at least a phosphorescence emission layer, wherein at least one in the constituent layer contains a compound represented by formula (1), (3) or (4). It is preferred that the phosphorescence emission layer or the hole inhibiting layer in the constituent layer contains the compound represented by formula (1), (3) or (4).

Examples of the substituent represented by $A_1$ or $A_2$ of formula (1), (2) or (4) include an alkyl group (preferably having 1 to 20 carbon atoms, more preferably 1 to 12 carbon atoms, and still more preferably 1 to 8 carbon atoms, such as methyl, ethyl, isopropyl, tert-butyl, n-octyl, n-decyl, n-hexyl, cyclopropyl, cyclopentyl, cyclohexyl, etc.); an alkenyl group (preferably having 2 to 20 carbon atoms, more preferably 2 to 12 carbon atoms, and still more preferably 2 to 8 carbon atoms, such as vinyl, allyl, 2-butenyl, 3-pentenyl, etc.); an alkynyl group (preferably having 2 to 20 carbon atoms, more preferably 2 to 12 carbon atoms, and still more preferably 2 to 8 carbon atoms, such as propargyl, 3-pentynyl, etc.); an aryl group (preferably having 6 to 30 carbon atoms, more preferably 6 to 20 carbon atoms, and still more preferably 6 to 12 carbon atoms, such as phenyl, p-methylphenyl, naphthyl, etc.); an amino group (preferably having 0 to 20 carbon atoms, more preferably 0 to 10 carbon atoms, and still more preferably 0 to 6 carbon atoms, such as amino, methylamino, dimethylamino, diethylamino, dibenzylamino, etc.); an alkoxy group (preferably having 1 to 20 carbon atoms, more preferably 1 to 12 carbon atoms, and still more preferably 1 to 8 carbon atoms, such as methoxy, ethoxy, butoxy, etc.), an aryloxy group (preferably having 6 to 20 carbon atoms, more preferably 6 to 16 carbon atoms, and still more preferably 6 to 12 carbon atoms, such as phenoxy, naphthoxy, etc.); an acyl group (preferably having 1 to 20 carbon atoms, more preferably 1 to 16 carbon atoms, and still more preferably 1 to 12 carbon atoms, such as acetyl, benzoyl, formyl, pivaloyl, etc.); an alkoxycarbonyl group (preferably having 2 to 20 carbon atoms, more preferably 2 to 16 carbon atoms, and still more preferably 2 to 12 carbon atoms, such as methoxycarbonyl, ethoxycarbonyl, etc.); an aryloxycarbonyl group preferably having 7 to 20 carbon atoms, more preferably 7 to 16 carbon atoms, and still more preferably 7 to 12 carbon atoms, such as phenyoxycarbonyl); an acyloxy group (preferably having 2 to 20 carbon atoms, more preferably 2 to 16 carbon atoms, and still more preferably 2 to 12 carbon atoms, such as acetoxy, benzoyloxy, etc.); an acylamino group (preferably having 2 to 20 carbon atoms, more preferably 2 to 16 carbon atoms, and still more preferably 2 to 12 carbon atoms, such as acetylamino, benzoylamino, etc.); an alkoxycarbonylamino group (preferably having 2 to 20 carbon atoms, more preferably 2 to 16 carbon atoms, and still more preferably 2 to 12 carbon atoms, such as methoxycarbonylamino), an aryloxycarbonylamino group (preferably having 7 to 20 carbon atoms, more preferably 7 to 16 carbon atoms, and still more preferably 7 to 12 carbon atoms, such as phenyloxycarbonylamino); a sulfonylamino group (preferably having 1 to 20 carbon atoms, more preferably 1 to 16 carbon atoms, and still more preferably 1 to 12 carbon atoms, such as methanesulfonylamino, benzenesulfonylamino, etc.); a sulfamoyl group (preferably having 0 to 20 carbon atoms, more preferably 0 to 16 carbon atoms, and still more preferably 0 to 12 carbon atoms, such as sulfamoyl, methylsulfamoyl, dimethylsulfamoyl, etc.); a carbamoyl group (preferably having 1 to 20 carbon atoms, more preferably 1 to 16 carbon atoms, and still more preferably 1 to 12 carbon atoms, such as carbamoyl, methylcarbamoyl, diethylcarbamoyl, phenylcarbamoyl, etc.); an alkylthio group (preferably having 1 to 20 carbon atoms, more preferably 1 to 16 carbon atoms, and still more preferably 1 to 12 carbon atoms, such as methylthio, ethylthio, etc.); an arylthio group (preferably having 6 to 20 carbon atoms, more preferably 6 to 16 carbon atoms, and still more preferably 6 to 12 carbon atoms, such as phenylthio, etc.); a sulfonyl group (preferably having 1 to 20 carbon atoms, more preferably 1 to 16 carbon atoms, and still more preferably 1 to 12 carbon atoms, such as mesyl, tosyl, etc.); a sulfinyl group (preferably having 1 to 20 carbon atoms, more preferably 1 to 16 carbon atoms, and still more preferably 1 to 12 carbon atoms, such as methanesulfinyl, benzenesulfinyl, etc.); a ureido group (preferably having 1 to 20 carbon atoms, more preferably 1 to 16 carbon atoms, and still more preferably 1 to 12 carbon atoms, such as ureido, methylureido, phenylureido); a phosphoramide group (preferably having 1 to 20 carbon atoms, more preferably 1 to 16 carbon atoms, and still more preferably 1 to 12 carbon atoms, such as diethylphosphoramide, phenylphosphoramide, etc.); a hydroxyl group; a halogen atom (e.g., fluorine, chlorine, bromine, iodine); a cyano group; a sulfo group; a carboxyl group; a nitro group; a hydroxamic acid group; a sulfino group; a hydrazino group; an imino group, and a heterocyclic group (a cyclic group containing a nitrogen atom, an oxygen atom, or a sulfur atom as a hetero atom and having preferably 1 to 30 carbon atoms, and more preferably 1 to 12 carbon atoms, such as imidazolyl, pyridyl, furyl, piperidyl, morpholino, etc. These substituents may further have a substituent. These substituents may combine with each other to form a ring, if possible.

In formula (1) above, $X_1$ represents an oxygen atom, a sulfur atom, an alkylene group, an imino group, a carbonyl group, a sulfoxide group or a sulfonyl group, and $X_2$ represents an oxygen atom, a sulfur atom, an alkylene group, an imino group, a carbonyl group, a sulfoxide group, a sulfonyl group, or a chemical bond.

In formula (1) above, $X_1$ is preferably an oxygen atom, a sulfur atom, a sulfonyl group or an alkylene group, and more preferably an oxygen atom, a sulfur atom or a sulfonyl group.

In formula (3) above, Y is preferably an oxygen atom, a sulfur atom or a sulfonyl group, and more preferably an oxygen atom.

In formula (1) above, $X_2$ is preferably an oxygen atom, a sulfur atom, a sulfonyl group, an alkylene group or a chemical bond and more preferably an oxygen atom, a sulfur atom, a sulfonyl group or a chemical bond.

In formula (3) above, Y is preferably an oxygen atom, a sulfur atom or a sulfonyl group, and more preferably an oxygen atom.

In formula (2), $Z_1$ and $Z_2$ represent an atomic group necessary to form an aromatic heterocyclic ring or an aromatic hydrocarbon ring. Examples of the aromatic heterocyclic ring include a furan ring, a thiophene ring, a pyridine ring, a pyridazine ring, a pyrimidine ring, a pyrazine ring, a triazine ring, a benzimidazole ring, an oxadiazole ring, a triazole ring, an imidazole ring, a pyrazole ring, a thiazole ring, an indole ring, a benzimidazole ring, a benzothiazole ring, a benzoxazole ring, a quinoxaline ring, a quinazoline ring, a phthalazine ring, a carbazole ring, a carboline ring and a diazacarbazole ring in which one carbon atom constituting a carboline ring is further replaced with a nitrogen atom. Examples of the aromatic hydrocarbon ring include a benzene ring, a biphenyl ring, a naphthalene ring, an azulene ring, an anthracene ring, a phenanthrene ring, a pyrene ring, a chrysene ring, a naphthacene ring, a triphenylene ring, an o-terphenyl ring, an m-terphenyl ring, a p-terphenyl ring, an acenaphthene ring, a coronene ring, a fluorene ring, a fluoranthene ring, a pentacene ring, a pentacene ring, a perylene ring, a pentaphene ring, a picene ring, a pyrene ring, a pyranthrene ring and an anthranthrene ring. These aromatic heterocyclic rings or aromatic hydrocarbon rings may have a substituent.

Examples of the divalent linkage group represented by $Z_3$ include a divalent hydrocarbon group such as alkylene, alkenylene, alkynylene or arylene; a divalent linkage group containing a hetero atom; a divalent linkage group derived from an aromatic heterocyclic compound (also referred to as a hetero aromatic compound) such as thiophene-2,5-diyl or pyrazine-2,3-diyl; a chalcogen atom such as an oxygen atom or a sulfur atom; and a divalent hydrocarbon group intervened by a hetero atom such as alkylimino, dialkylsilanediyl or diarylgermanediyl. The chemical bond refers to a chemical bond combining substituents directly.

Typical examples of compounds represented by formulae (1), (3) and (4) will be listed below, but the invention is not limited thereto.

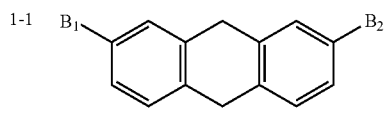 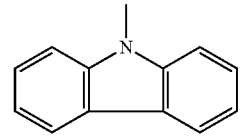

-continued
| | | $B_1, B_2$ |
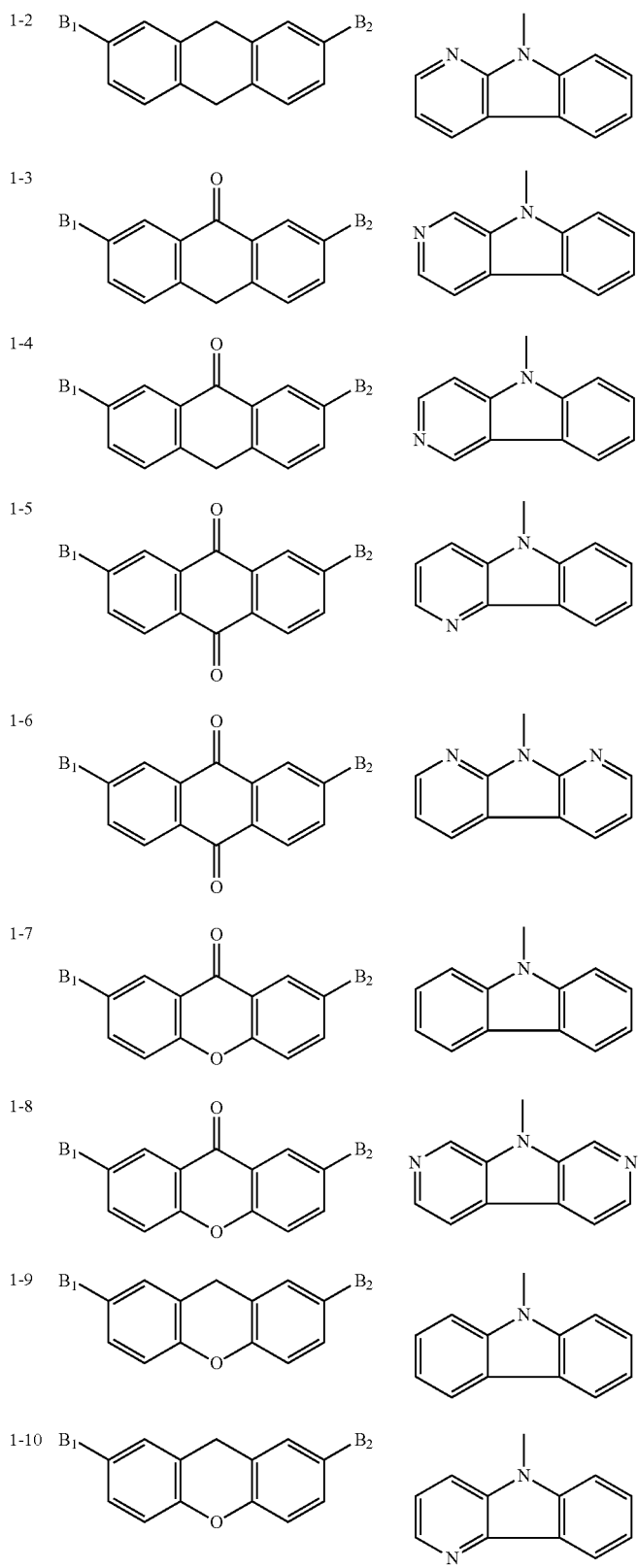

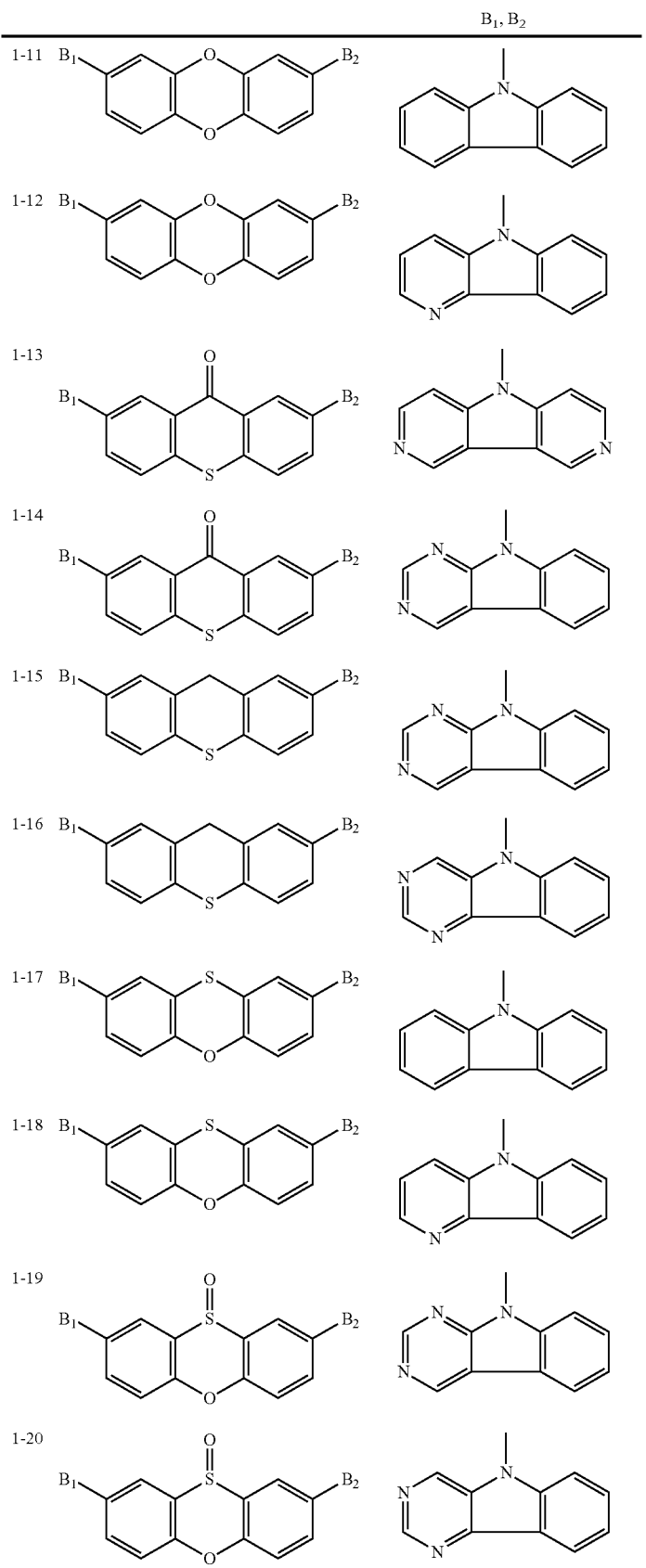

|   | B₁, B₂ |   |
|---|---|---|
| 1-21 | 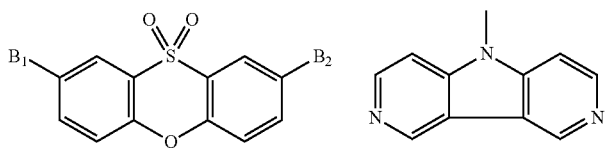 | 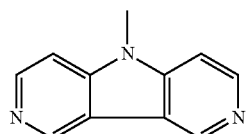 |
| 1-22 | 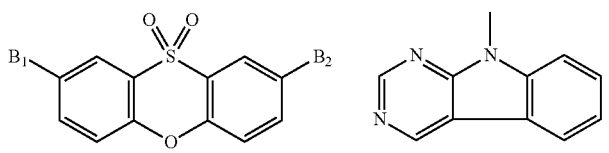 | 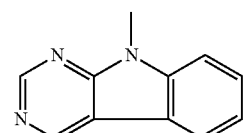 |
| 1-23 | 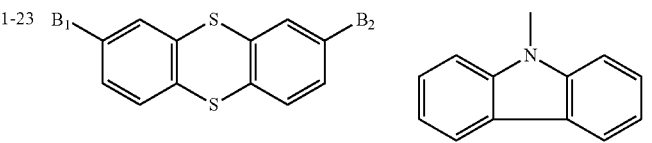 | 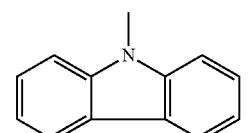 |
| 1-24 | 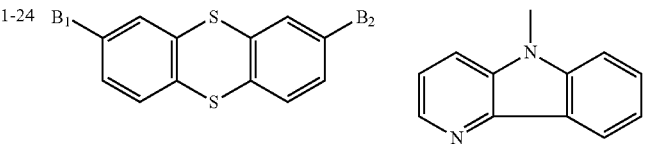 | 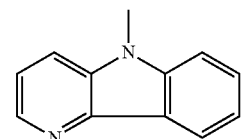 |
| 1-25 | 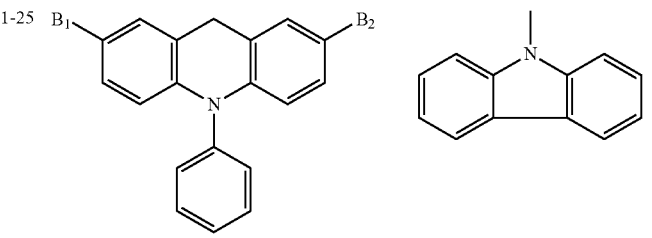 | 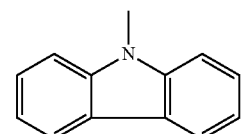 |
| 1-26 | 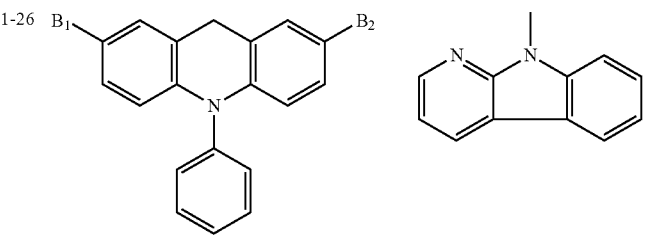 | 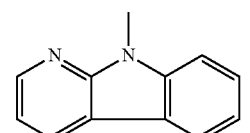 |
| 1-27 | 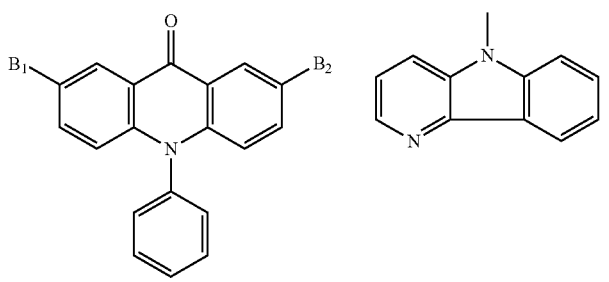 | 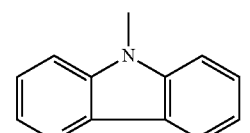 |

-continued
| | | $B_1, B_2$ |
|---|---|---|
| 1-28 | 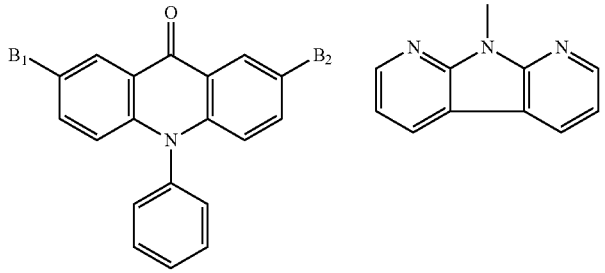 | 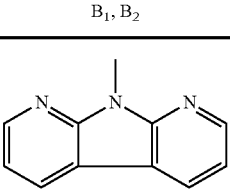 |
| 3-1 | 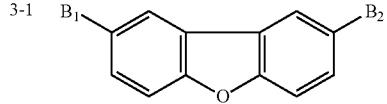 | 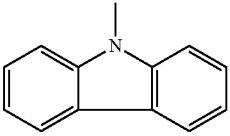 |
| 3-2 | 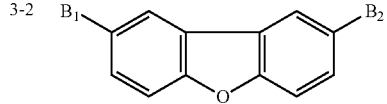 | 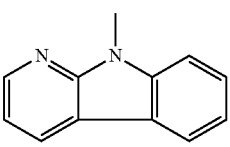 |
| 3-3 | 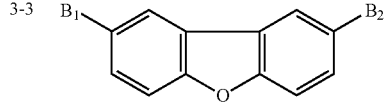 | 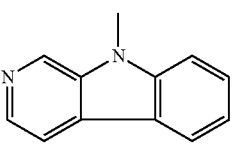 |
| 3-4 | 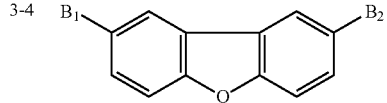 | 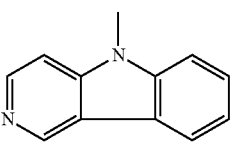 |
| 3-5 | 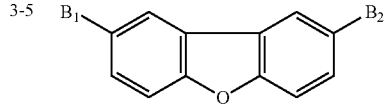 | 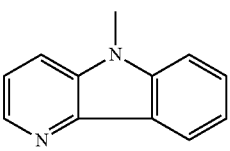 |
| 3-6 | 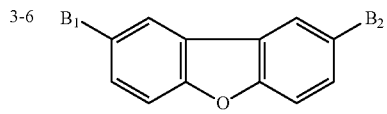 | 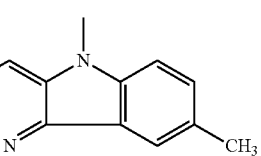 |
| 3-7 | 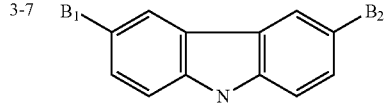 | 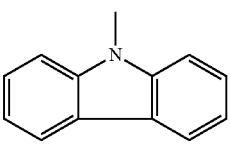 |

-continued
|   | B₁, B₂ |
|---|---|
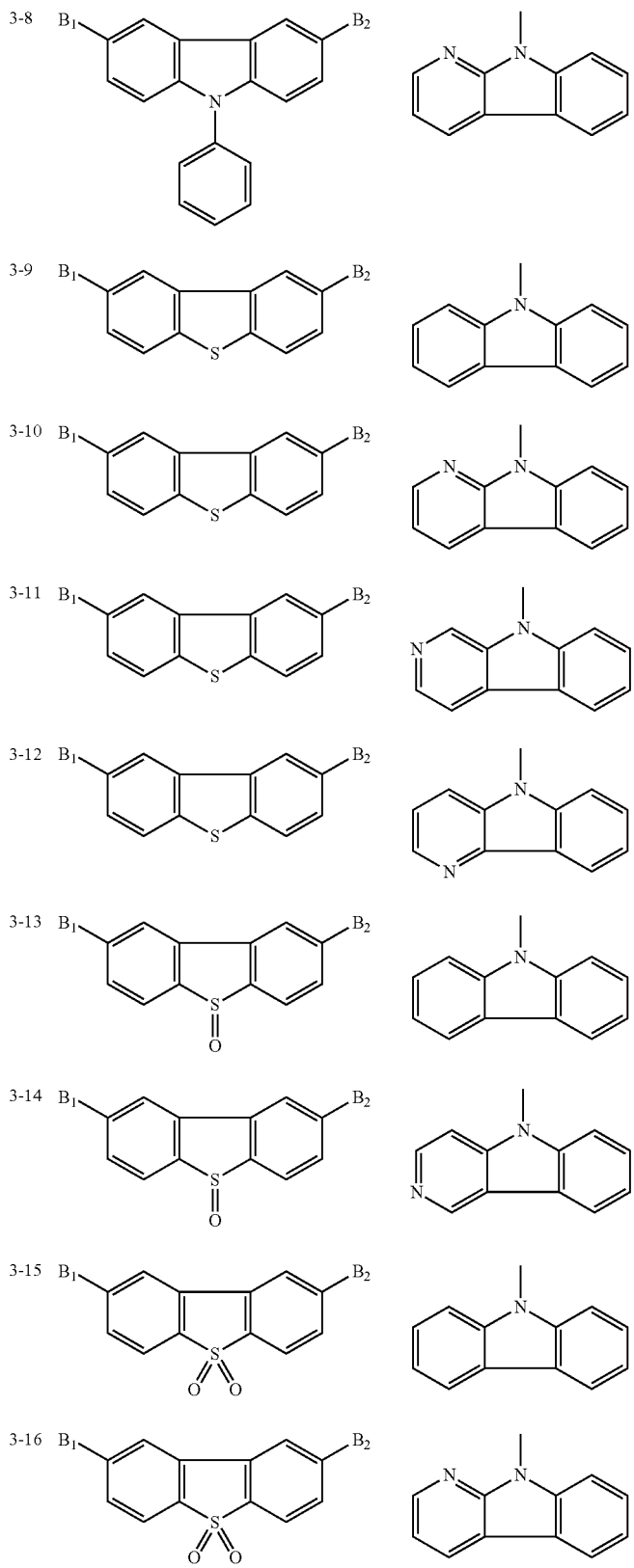

Representative synthetic examples of the compound invention will be shown below, but the invention is not limited thereto.

SYNTHETIC EXAMPLE 1

Preparation of Exemplified Compound 1-9

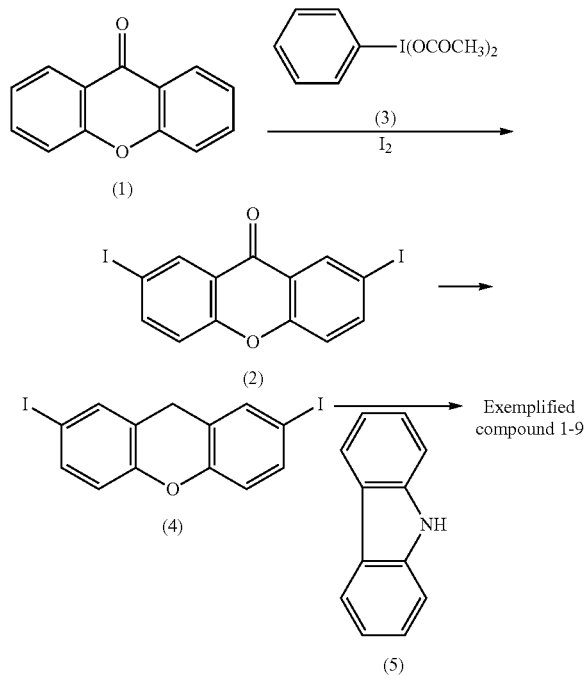

Compound (3) of 22 g and 16 g of iodine were added to a solution of 90 ml of acetic acid and 90 ml of acetic anhydride, 12 g of Compound (1) were added thereto in five minutes, and two or three drops of sulfuric acid were added. The resulting mixture was stirred for 30 minutes. The reaction mixture was poured into 600 ml of an aqueous 5% sodium sulfite solution, added with 5 g of sodium carbonate, and filtered under reduced pressure to obtain crude product. The resulting product was suspended in 300 ml of acetone while heating, and filtered under reduced pressure to obtain 3.5 g of Compound (2) (yield 12.7%).

Subsequently, 2.7 g of Compound (2) were dissolved in 70 ml of THF, and 0.91 g of $NaBH_4$ was slowly added to the solution. The resulting solution was cooled with ice water, dropwise added with 1.1 ml of dimethyl sulfate in 15 minutes, and stirred at room temperature for 4 hours. The reaction mixture was washed with a saturated sodium chloride solution and the solvent was removed under reduced pressure to obtain a residue. The residue was recrystallized from methanol to obtain 1.5 g of Compound (4) (yield 58%).

Palladium acetate of 0.091 g and 3.2 ml of a 10% tri-tert-butylphosphine xylene solution were mixed at 50 to 60° C. for 30 minutes under nitrogen atmosphere. Subsequently, 40 ml of anhydrous xylene, 1.5 g of Compound (4), 1.21 g of Compound (5) and 0.78 g of sodium t-butylate were added to the mixture and refluxed for 15 hours. The resulting reaction mixture was concentrated under reduced pressure and added with THF and filtered to remove undissolved substances. The filtrate was concentrated under reduced pressure to obtain crude product. The crude product was purified according to GPC (eluting solvent: THF), suspended in hexane while heating to obtain Exemplified compound 1-9. The yield was 0.50 g (29.0%). The chemical structure of the compound was identified according to $^1$H-NMR spectra and mass spectroscopy analysis.

SYNTHETIC EXAMPLE 2

Preparation of Exemplified Compound 3-1

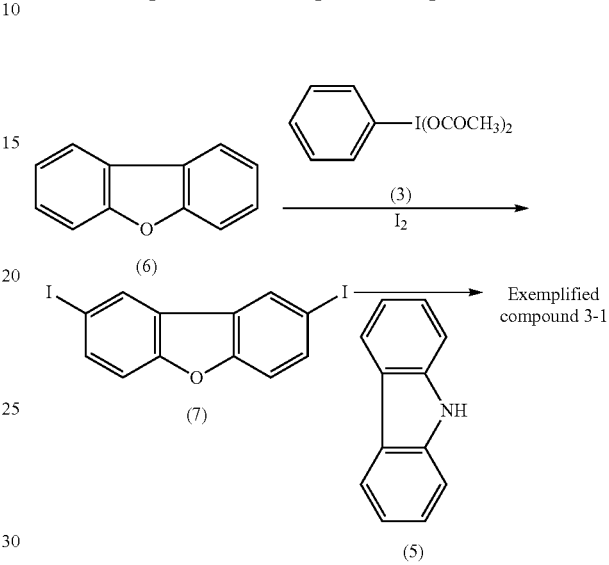

Compound (3) of 6.3 g and 4.7 g of iodine were added to a solution of 22 ml of acetic acid and 22 ml of acetic anhydride, 3 g of Compound (6) were added thereto in five minutes, and two or three drops of sulfuric acid were added. The resulting mixture was stirred for 20 minutes. The reaction mixture was poured into 300 ml of an aqueous 5% sodium sulfite solution, added with 1 g of sodium carbonate, and filtered under reduced pressure to obtain crude product.

The resulting product was recrystallized from chloroform to obtain to obtain 4.7 g of Compound (7) (yield 62.2%).

Palladium acetate of 0.091 g and 3.20 ml of a 10% tri-tert-butylphosphine xylene solution were mixed at 50 to 60° C. for 30 minutes under nitrogen atmosphere. Subsequently, 40 ml of anhydrous xylene; 1.5 g of Compound (7), 1.3 g of Compound (5) and 0.78 g of sodium t-butylate were added to the mixture and refluxed for 5 hours. The resulting reaction mixture was concentrated under reduced pressure and added with THF and filtered to remove undissolved substances. The filtrate was concentrated under reduced pressure to obtain crude product. The crude product was purified according to column chromatography (silica gel, eluting solvent: methylene chloride), and further crystallized from toluene to obtain Exemplified compound 3-1. The yield was 0.80 g (44.9%). The chemical structure of the compound was identified according to $^1$H-NMR spectra and mass spectroscopy analysis.

The compounds represented by formula (1), (2) or (4) in the invention are used as materials for an organic EL device (for example, a back light, a flat panel display, a light source of an illumination, a display device, a light source for electrophotography, a recording light source, an exposure light source, a reading light source, a sign, a signboard, an interior, or an optical-transmission device). Examples of other usage include extended fields such as: materials for an organic semiconductor laser (for example, a recording light source, an exposure light source, a reading light source, an optical transmission device and a light source for electrophotography); materials for a photoreceptor for electrophotography; materials for an organic TFT element (for example, an organic memory device, an organic operation device, an organic switching element); materials for an organic wavelength converter; and materials for a photoelectric conversion device (for example, a solar cell, a photosensor).

In the invention, preferred examples of the constituent layer of the organic EL device of the invention will be shown below, but the invention is not limited thereto.

(i): Anode/Light emission layer/Electron transporting layer/Cathode (ii): Anode/Hole transporting layer/Light emission layer/Electron transporting layer/Cathode (iii): Anode/Hole transporting layer/Light emission layer/Hole blocking layer/Electron transporting layer/Cathode (iv): Anode/Hole transporting layer/Light emission layer/Hole blocking layer/Electron transporting layer/Cathode buffering layer/Cathode (v): Anode/Anode buffering layer/Hole transporting layer/Light emission layer/Hole blocking layer/Electron transporting layer/Cathode buffering layer/Cathode A hole transporting layer is preferably adjacent to an anode, and an electron hole transporting layer is preferably adjacent to a cathode, <<Anode>>

For the anode of the organic EL device, a metal, an alloy, or an electroconductive compound each having a high working function (not less than 4 eV), and mixture thereof are preferably used as the electrode material. Concrete examples of such an electrode material include a metal such as Au, and a transparent electroconductive material such as CuI, indium tin oxide (ITO), $SnO_2$, or ZnO, and a material capable of forming an amorphous and transparent conductive layer such as IDIXO ($In_2O_3$—ZnO). The anode may be prepared by forming a thin layer of the electrode material according to a depositing or spattering method, and by forming the layer into a desired pattern according to a photolithographic method. When required precision of the pattern is not so high (not less than 100 µm), the pattern may be formed by depositing or spattering of the electrode material through a mask having a desired form. When light is emitted through the anode, the transmittance of the anode is preferably 10% or more, and the sheet resistance of the anode is preferably not more than several hundred Ω/□. The thickness of the layer is ordinarily within the range of from 10 nm to 1 µm, and preferably from 10 to 200 nm, although it may vary due to kinds of materials used.

<<Cathode>>

On the other hand, for the cathode, a metal (also referred to as an electron injecting metal), an alloy, and an electroconductive compound each having a low working function (not more than 4 eV), and a mixture thereof is used as the electrode material. Concrete examples of such an electrode material include sodium, sodium-potassium alloy, magnesium, lithium, a magnesium/copper mixture, a magnesium/silver mixture, a magnesium/aluminum mixture, magnesium/indium mixture, an aluminum/aluminum oxide ($Al_2O_3$) mixture, indium, a lithium/aluminum mixture, and a rare-earth metal. Among them, a mixture of an electron injecting metal and a metal higher in the working function than that of the electron injecting metal, such as the magnesium/silver mixture, magnesium/aluminum mixture, magnesium/indium mixture, aluminum/aluminum oxide ($Al_2O_3$) mixture, lithium/aluminum mixture, or aluminum is suitable from the view point of the electron injecting ability and resistance to oxidation. The cathode can be prepared forming a thin layer of such an electrode material by a method such as a deposition or spattering method. The sheet resistance as the cathode is preferably not more than several hundred Ω/□, and the thickness of the layer is ordinarily from 10 nm to 1 µm, and preferably from 50 to 200 nm. It is preferable in increasing the light emission efficiency that either the anode or the cathode of the organic EL device is transparent or semi-transparent.

After a layer of the metal described above as a cathode is formed to give a thickness of from 1 to 20 nm, a layer of the transparent electroconductive material as described in the anode is formed on the resulting metal layer, whereby a transparent or semi-transparent cathode can be prepared. Employing the cathode, a device can be manufactured in which both anode and cathode are transparent.

Next, an injecting layer, a blocking layer, and an electron transporting layer used in the component layer of the organic EL device of the invention will be explained.

<<Injecting Layer: Electron Injecting Layer, Hole Injecting Layer>>

The injecting layer is optionally provided, for example, an electron injecting layer or a hole injecting layer, and may be provided between the anode and the light emission layer or hole transporting layer, and between the cathode and the light emission layer or electron transporting layer as described above.

The injecting layer herein referred to is a layer provided between the electrode and an organic layer in order to reduce the driving voltage or to improve of light emission efficiency. As the buffer layer there are a hole injecting layer (an anode buffer layer) and an electron injecting layer (a cathode buffer layer), which are described in "Electrode Material" page 123, Div. 2 Chapter 2 of "Organic EL device and its frontier of industrialization" (published by NTS Corporation, Nov. 30, 1998) in detail.

The anode buffer layer (hole injecting layer) is described in Japanese Patent O.P.I. Publication Nos. 9-45479, 9-260062, and 8-288069 etc., and its examples include a phthalocyanine buffer layer represented by a copper phthalocyanine layer, an oxide buffer layer represented by a vanadium oxide layer, an amorphous carbon buffer layer, a polymer buffer layer employing an electroconductive polymer such as polyaniline (emeraldine), and polythiophene, etc.

The cathode buffer layer (electron injecting layer) is described in Japanese Patent O.P.I. Publication Nos. 6-325871, 9-17574, and 9-74586, etc. in detail, and its examples include a metal buffer layer represented by a strontium or aluminum layer, an alkali metal compound buffer layer represented by a lithium fluoride layer, an alkali earth metal compound buffer layer represented by a magnesium fluoride layer, and an oxide buffer layer represented by an aluminum oxide. The buffer layer (injecting layer) is preferably very thin and has a thickness of preferably from 0.1 to 100 nm depending on kinds of the material used.

<<Inhibiting Layer: Hole Inhibiting Layer, Electron Inhibiting Layer>>

The inhibiting layer is a layer provided if necessary in addition to the fundamental constituent layer as described above, and is for example a hole inhibiting layer as described in Japanese Patent O.P.I. Publication Nos. 11-204258, and 11-204359, and on page 237 of "Organic EL device and its frontier of industrialization" (published by NTS Corporation, Nov. 30, 1998).

The hole inhibiting layer is an electron transporting layer in a broad sense, and is comprised of material having an ability of transporting electrons but an extremely poor ability of holes, which can increase a recombination probability of electrons and holes by transporting electrons and blocking holes.

In the organic EL device of the invention, a hole inhibiting layer is adjacent to a light emission layer.

In the invention, the hole inhibiting layer preferably contains as a hole inhibiting material the compound in the invention as described above, whereby an organic EL device having further higher emission efficiency and further longer lifetime can be obtained.

On the other hand, the electron blocking layer is an hole transporting layer in a broad sense, and is comprised of material having an ability of transporting holes but an extremely poor ability of electrons, which can increase a recombination probability of electrons and holes by transporting holes and blocking electrons.

<<Light Emission Layer>>

The light emission layer in the invention is a layer where electrons and holes, injected from electrodes, an electron transporting layer or a hole transporting layer, are recombined to emit light. The portions where light emits may be in the light emission layer or at the interface between the light emission layer and the layer adjacent thereto.

It is preferred in the invention that the light emission layer contains a host compound described later and a phosphorescent compound (also referred to a phosphorescence emitting compound). In the invention, the compound in the invention as described above is preferably used as the host compound, whereby an organic EL device having further higher emission efficiency can be obtained. A compound other than the compound in the invention as described above may be used as a host.

Herein, the host compound in the invention is defined as a compound in the light emission layer having a phosphorescence quantum yield at room temperature (25° C.) of less than 0.01.

Plural known host compounds may be used. Usage of plural host compounds can adjust charge transfer, and obtain an organic EL device with high efficiency. Usage of plural phosphorescent compounds can mix light with a different color, and can emit light with any color. A white light emission can be emitted by selecting kinds of the phosphorescent compound or a doping amount of the phosphorescent compounds, which can be applied for an illuminating lamp or a back light.

The known host compound is preferably a compound with high Tg (glass transition temperature), which has a hole and electron transporting ability, and prevents the emission wavelength shifting to longer wavelength.

Typical examples of the host compound include those described in the following Documents.

For example, JP-A Nos. 2001-257076, 2002-308855, 2001-313179, 2001-319491, 2001-357977, 2002-334736, 2002-8860, 2002-334787, 2002-15871, 2002-334788, 2002-43056, 2002-334789, 2002-75645, 2002-338579, 2002-105445, 2002-343568, 2002-141173, 2002-352957, 2002-203683, 2002-363227, 2002-231453, 2003-3165, 2002-234888, 2003-27048, 2002-255934, 2002-260861, 2002-280183, 2002-299060, 2002-302516, 2002-305083, 2002-305084 and 2002-308837.

The light emission layer may contain a fluorescence emission compound having a wavelength providing a fluorescence maximum. In this case, electroluminescence as an organic EL device is emitted from the fluorescence emission compound to which energy is transferred from a host compound and a phosphorescent compound. The preferred fluorescent compound is one having a high fluorescence quantum yield in the form of solution. Herein, the fluorescence quantum yield is preferably not less than 10%, and more preferably not less than 30%. Examples of the phosphorescent compound include a coumarin dye, a cyanine dye, a chloconium dye, a squalenium dye, an oxobenzanthracene dye, a fluorescene dye, a rhodamine dye, a pyrylium dye, a perylene dye, a stilbene dye, and a polythiophene dye. The fluorescence quantum yield can be measured according to a method described in the fourth edition, Jikken Kagaku Koza 7, Bunko II, p. 362 (1992) (published by Maruzen).

Phosphorescent Compound (Phosphorescence Emission Compound)

As a material (hereinafter also referred to as a light emission material) used in the light emission layer, a phosphorescent compound is preferably used in addition to the host compound as described above, whereby an organic EL device with high emission efficiency can be obtained.

The phosphorescent compound in the invention is a compound which emits light from the excited triplet, can emit phosphorescence at room temperature (25° C.), and has a phosphorescent quantum yield at 25° C. of not less than 0.01. The phosphorescent quantum yield at 25° C. is preferably not less than 0.1. The phosphorescent quantum yield can be measured according to a method described in the fourth edition "Jikken Kagaku Koza 7", Bunko II, page 398 (1992) published by Maruzen. The phosphorescent quantum yield can be measured in a solution employing various kinds of solvents. The phosphorescent compound used in the invention is a compound, in which the phosphorescent quantum yield measured employing any one of the solvents falls within the above-described range.

The light emission of the phosphorescent compound is divided in two types in principle, one is an energy transfer type in which recombination of a carrier occurs on the host to which the carrier is transported to excite the host, the resulting energy is transferred to the phosphorescent compound, and light is emitted from the phosphorescent compound, and the other is a carrier trap type in which recombination of a carrier occurs on the phosphorescent compound, a carrier trap material, and light is emitted from the phosphorescent compound. However, in each type, energy level of the phosphorescent compound in excited state is lower than that of the host in excited state.

The phosphorescent compound is suitably selected from those used in the light emission layer of an organic EL device.

The phosphorescent compound used in the invention is preferably a metal complex containing a metal belonging to groups 8 through 10 of the periodic table as a center metal, and is more preferably an iridium compound, an osmium compound, a platinum compound (a platinum complex) or a rare earth compound, and most preferably an iridium compound.

Examples of the phosphorescent compound used in the invention will be listed below, but the invention is not limited thereto. These compounds can be synthesized according to a method described in Inorg. Chem. Vol. 40, 1704-1711.

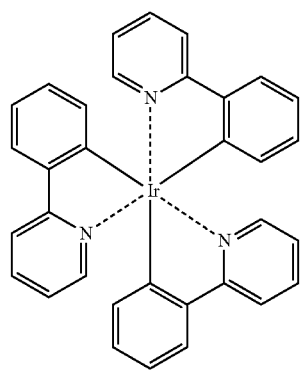

Ir-1

-continued
Ir-2
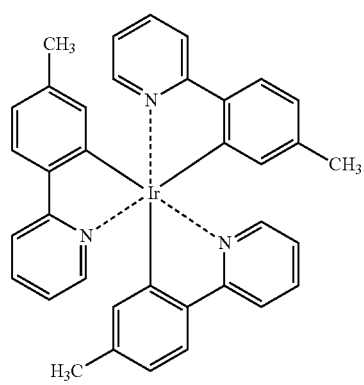
Ir-3
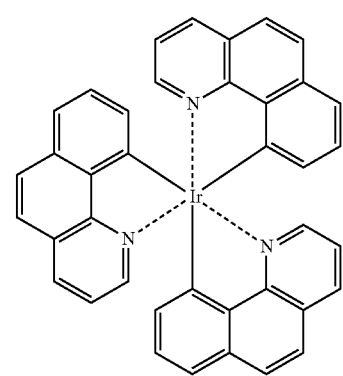
Ir-4
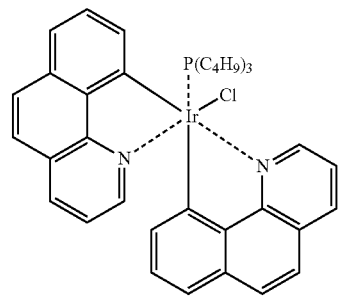
Ir-5
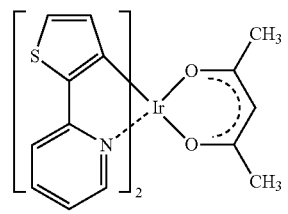
Ir-6
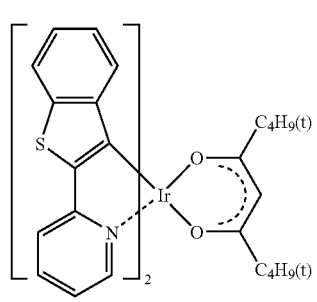
-continued
Ir-7
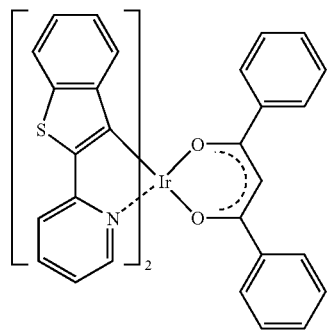
Ir-8
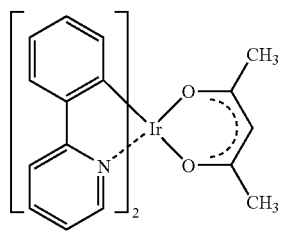
Ir-9
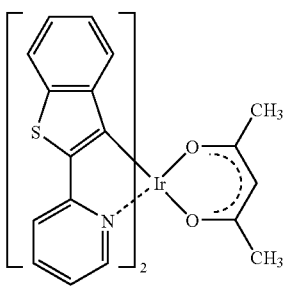
Ir-10
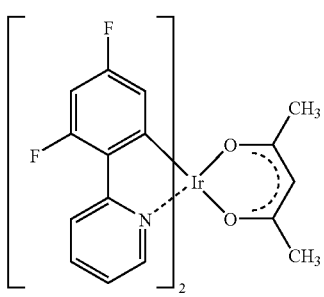
Ir-11
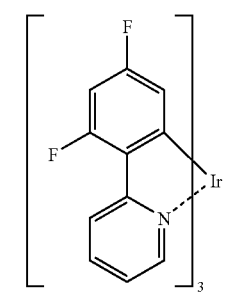

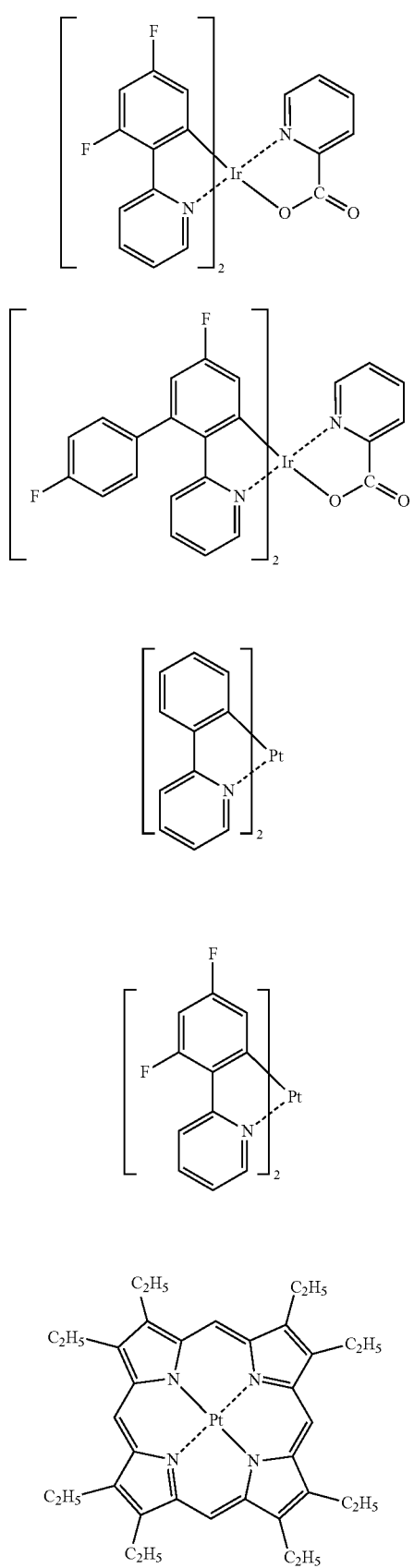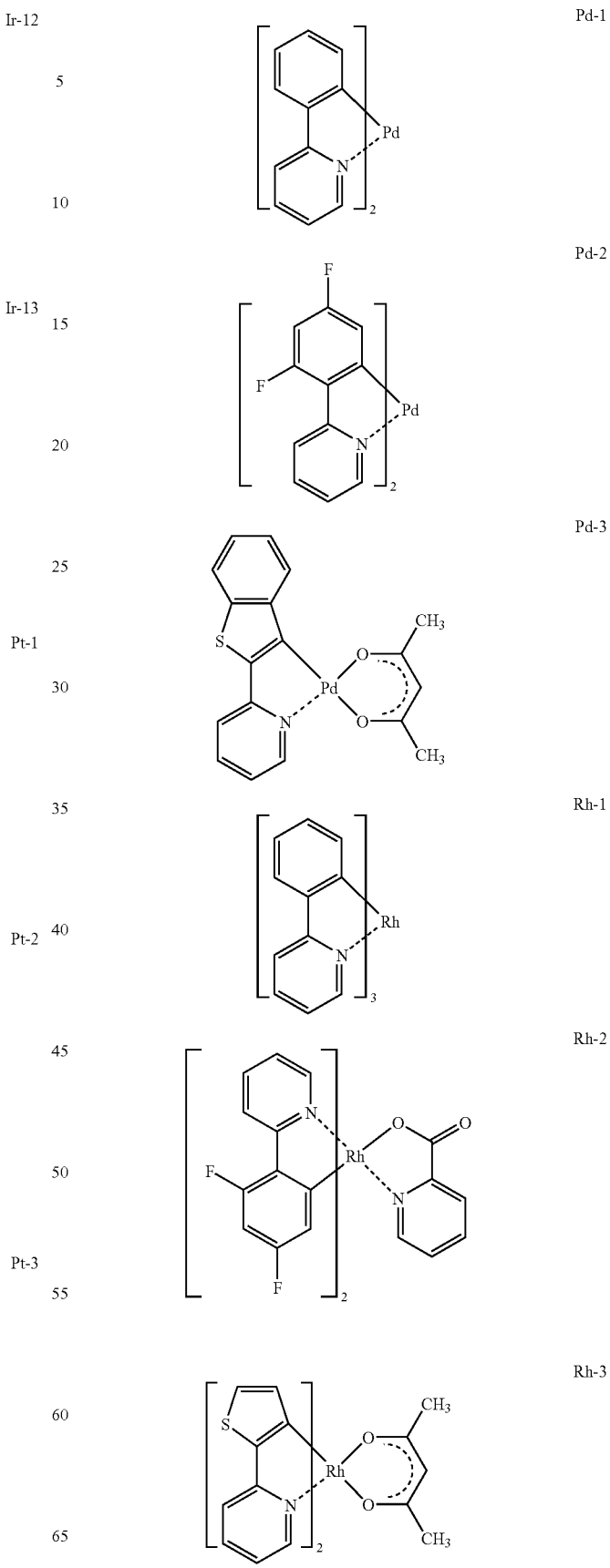

A-1
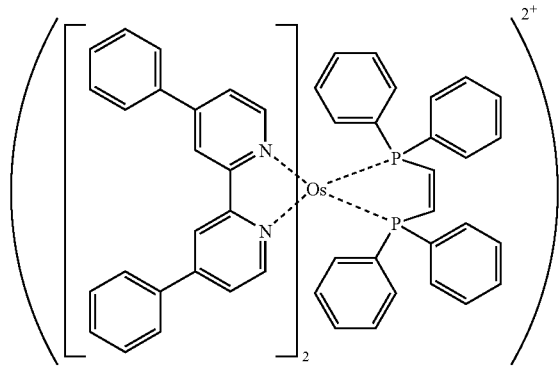
(CF₃CF₂CF₂COO⁻)₂

D-1
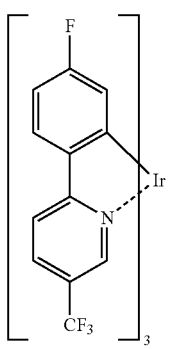

D-2
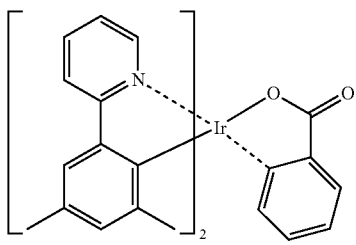

D-3
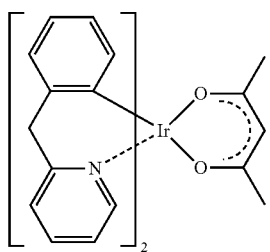

D-4
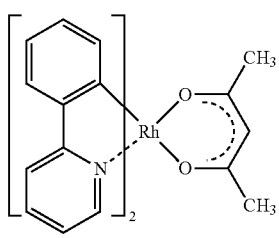

D-5
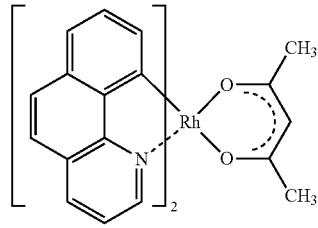

D-6
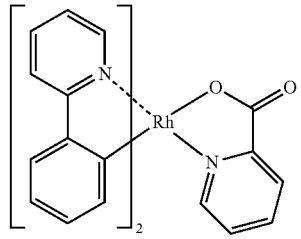

In the invention, the maximum phosphorescence wavelength of the phosphorescent compound is not specifically limited. Theoretically, the phosphorescence wavelength can be varied by selecting a center metal, a ligand, or a substituent of the ligand of complexes used. The phosphorescent compound is preferably a phosphorescent compound having a wavelength providing a phosphorescence maximum in the wavelength regions of from 380 to 480 nm. Such an organic electroluminescent device emitting a blue or white light phosphorescence can provide higher emission efficiency.

Figure 4:
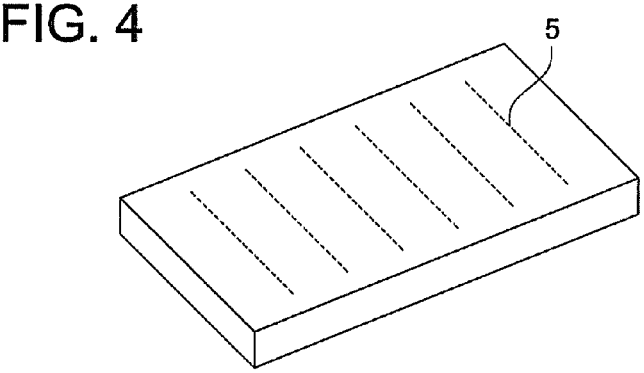
FIG. 4 is a schematic drawing of a display employing a passive matrix method.
Figure 4:
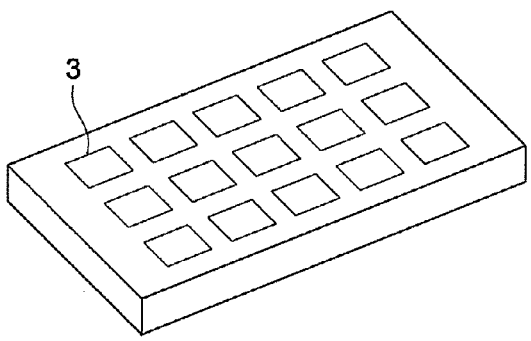
Figure 4:
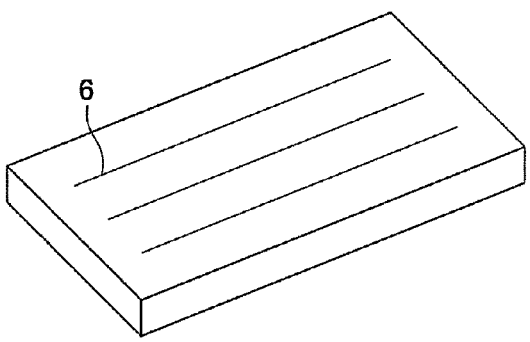

Color of light emitted from the organic EL device of the invention or the compound in the invention is measured by a spectral light meter CS-1000, manufactured by Minolta Co., Ltd., and expressed according to CIE chromaticity diagram described in FIG. 4.16 on page 108 of "Shinpen Shikisai Kagaku Handbook" (Coloring Science Handbook, New Edition), edited by Nihon Shikisai Gakkai, published by Todai Shuppan Kai, 1985.

The light emission layer can be formed employing the above-described compounds and a known method such as a vacuum deposition method, a spin coat method, a casting method, an LB method or an ink jet method. The thickness of the light emission layer is not specifically limited, but is ordinarily from 5 nm to 5 μm, and preferably from 5 to 200 nm. The light emission layer may be composed of a single layer comprising one or two or more of the phosphorescent compound or the host compound, or of plural layers comprising the same composition or different composition.

<<Hole Transporting Layer>>

The hole transporting layer is comprised of a hole transporting material having an ability of transporting holes, and a hole injecting layer and an electron blocking layer are included in the hole transporting layer in a broad sense. The hole transporting layer may be a single layer or plural layers.

The hole transporting material has a hole injecting ability, a hole transporting ability or an ability to form a barrier to electrons, and may be either an organic substance or an inorganic substance. Examples of thereof include a triazole derivative, an oxadiazole derivative, an imidazole derivative, a polyarylalkane derivative, a pyrazoline derivative and a pyrazolone derivative, a phenylenediamine derivative, an arylamine derivative, an amino substituted chalcone derivative, an oxazole derivative, a styryl anthracene derivative, a fluorenone derivative, a hydrazone derivative, a stilbene derivative, a silazane derivative, an aniline copolymer, and an electroconductive oligomer, particularly a thiophene oligomer.

As the hole transporting material, those described above are used, but a porphyrin compound, an aromatic tertiary amine compound, or a styrylamine compound is preferably used, and an aromatic tertiary amine compound is more preferably used.

Typical examples of the aromatic tertiary amine compound and styrylamine compound include N,N,N',N'-tetraphenyl-4,4'-diaminophenyl, N,N'-diphenyl-N,N'-bis(3-methylphenyl)-[1,1'-biphenyl]-4,4'-diamine (TPD), 2,2'-bis(4-di-p-tolylaminophenyl)propane, 1,1'-bis(4-di-p-tolylaminophenyl)cyclohexane, N,N,N',N'-tetra-p-tolyl-4,4'-diaminobiphenyl, 1,1'-bis(4-di-p-tolylaminophenyl)-4-phenylcyclohexane, bis(4-dimethylamino-2-methylphenyl)-phenylmethane, bis(4-di-p-tolylaminophenyl)-phenylmethane, N,N'-diphenyl-N,N'-di(4-methoxyphenyl)-4,4'-diaminobiphenyl, N,N,N',N'-tetraphenyl-4,4'-diaminodiphenylether, 4,4'-bis(diphenylamino) quardriphenyl, N,N,N-tri(p-tolyl)amine, 4-(di-p-tolylamino)-4'-[4-(di-p-tolylamino)styryl]stilbene, 4-N,N-diphenylamino-(2-diphenylvinyl)benzene, 3-methoxy-4'-N,N-diphenylaminostylbenzene, N-phenylcarbazole, compounds described in U.S. Pat. No. 5,061,569 which have two condensed aromatic rings in the molecule thereof such as 4,4'-bis[N-(1-naphthyl)-N-phenylamino]biphenyl (NPD), and compounds described in Japanese Patent O.P.I. Publication No. 4-308688 such as 4,4',4"-tris[N-(3-methylphenyl)-N-phenylamino]-triphenylamine (MTDATA) in which three triphenylamine units are bonded in a starburst form.

A polymer in which the material mentioned above is introduced in the polymer chain or a polymer having the material as the polymer main chain can be also used. As the hole injecting material or the hole transporting material, inorganic compounds such as p-Si and p-SiC are usable.

The hole transporting layer can be formed by layering the hole transporting material by a known method such as a vacuum deposition method, a spin coat method, a casting method, an ink jet method, and an LB method. The thickness of the hole transporting layer is not specifically limited, but is ordinarily from 5 to 5000 nm. The hole transporting layer may be composed of a single layer structure comprising one or two or more of the materials mentioned above.

<<Electron Transporting Layer>>

The electron transporting layer comprises a material (an electron transporting material) having an electron transporting ability, and in a broad sense refers to an electron injecting layer or a hole blocking layer. The electron transporting layer can be provided as a single layer or plural layers.

An electron transporting material (which serves also as a hole inhibiting material) used in a single electron transporting layer or in the electron transporting layer closest to the cathode in plural electron transporting layers has a function of incorporating electrons injected from a cathode to a light emission layer, and is selected from known compounds. Examples thereof include a nitro-substituted fluorene derivative, a diphenylquinone derivative, a thiopyran dioxide derivative, a carbodiimide, a fluorenylidenemethane derivative, an anthraquinodimethane, an anthrone derivative, and an oxadiazole derivative. Moreover, a thiadiazole derivative which is formed by substituting the oxygen atom in the oxadiazole ring of the foregoing oxadiazole derivative with a sulfur atom, and a quinoxaline derivative having a quinoxaline ring known as an electron withdrawing group are usable as the electron transporting material. A polymer in which the material mentioned above is introduced in the polymer side chain or a polymer having the material as the polymer main chain can be also used.

A metal complex of an 8-quinolynol derivative such as aluminum tris-(8-quinolynol) ($Alq_3$), aluminum tris-(5,7-dichloro-8-quinolynol), aluminum tris-(5,7-dibromo-8-quinolynol), aluminum tris-(2-methyl-8-quinolynol), aluminum tris-(5-methyl-8-quinolynol), or zinc bis-(8-quinolynol) ($Znq_2$), and a metal complex formed by replacing the central metal of the foregoing complexes with another metal atom such as In, Mg, Cu, Ca, Sn, Ga or Pb, can be used as the electron transporting material. Furthermore, a metal free or metal-containing phthalocyanine, and a derivative thereof, in which the molecular terminal is replaced by a substituent such as an alkyl group or a sulfonic acid group, are also preferably used as the electron transporting material. The distyrylpyrazine derivative exemplified as a material for the light emission layer may preferably be employed as the electron transporting material. An inorganic semiconductor such as n-Si and n-SiC may also be used as the electron transporting material in a similar way as in the hole transporting layer.

The electron transporting layer can be formed employing the above-described electron transporting materials and a known method such as a vacuum deposition method, a spin coat method, a casting method, a printing method including an ink jet method or an LB method. The thickness of electron transporting layer is not specifically limited, but is ordinarily from 5 nm to 5 μm, and preferably from 5 to 200 nm. The electron transporting layer may be composed of a single layer comprising one or two or more of the electron transporting material.

<<Substrate>>

The organic EL device of the invention is preferably provided on a substrate.

The substrate employed for the organic electroluminescent device of the invention is not restricted to specific kinds of materials such as glass and plastic, as far as it is transparent. Examples of the substrate preferably used include glass, quartz and light transmissible plastic film. Especially preferred one is a resin film capable of providing flexibility to the organic EL device.

Examples of the resin film include films of polyethylene terephthalate (PET), polyethylene naphthalate (PEN), polyethersulfone (PES), polyetherimide, polyetheretherketone, polyphenylene sulfide, polyarylate, polyimide, polycarbonate (PC), cellulose triacetate (TAC), cellulose acetate propionate (CAP) and so on. The surface of the resin film may have a layer of an inorganic or organic compound or a hybrid layer of both compounds.

The external light emission efficiency of the organic electroluminescent device of the invention is preferably not less than 1%, and more preferably not less than 5% at room temperature. Herein, external quantum yield (%) is represented by the following formula:

$$\text{External quantum yield (\%)} = (\text{the number of photons emitted to the exterior of the organic electroluminescent device} \times 100)/(\text{the number of electrons supplied to the organic electroluminescent device})$$

A hue improving filter such as a color filter may be used in combination or a color conversion filter which can convert from emission light color from an organic EL device to multi-color employing a fluorescent compound may be used in combination. In the case where the color conversion filter, the λmax of the light emitted from the organic EL device is preferably not more than 480 nm.

<<Preparation of Organic EL Device>>

For one example, the preparation of the organic EL device, which has the constitution, Anode/Hole injecting layer/Hole transporting layer/Light emission layer/Electron transporting layer/Electron injecting layer/Cathode, will be described.

A thin layer of a desired material for an electrode such as a material of the anode is formed on a suitable substrate by a deposition or sputtering method to prepare the anode, so that the thickness of the layer is not more than 1 μm, and preferably within the range of from 10 to 200 nm. Then the hole injecting layer, the hole transporting layer, the light emission layer, the electron transporting layer and the electron injecting layer, which constitute the organic EL device, are formed on the resulting anode in that order as organic compound thin layers.

As methods for formation of the thin layers, there are a spin coating method, a casting method, an ink jet method, a vacuum deposition method, and a printing method, however, a spin coating method and a vacuum deposition method are preferably used, since a uniform layer can be formed and a pinhole is formed with difficulty. Different methods may be used for formation of different layers. When the vacuum deposition method is used for the thin layer formation method, although conditions of the vacuum deposition differs due to kinds of materials used, vacuum deposition is preferably carried out at a boat temperature of from 50° C. to 450° C., at a degree of vacuum of from $10^{-6}$ to $10^{-2}$ Pa, at a deposition speed of from 0.01 to 50 nm/second, and at a substrate temperature of from −50 to 300° C. to form a layer with a thickness of from 0.1 nm to 5 μm.

After these layers has been formed, a thin layer comprised of a material for a cathode is formed thereon to prepare a cathode, employing, for example, a deposition method or sputtering method to give a thickness of not more than 1 μm, and preferably from 50 to 200 nm. Thus, a desired organic EL device is obtained. It is preferred that the layers from the hole injecting layer to the cathode are continuously formed under one time of vacuuming to obtain an organic EL device. However, on the way of the layer formation under vacuum a different layer formation method may be inserted. When the different method is used, its process is required to be carried out under a dry inert gas atmosphere.

In the multicolor display of the invention, the light emission layer only is formed using a shadow mask, and other layers than the light emission layer are common, and can be formed employing a vacuum method, a casting method, a spin coat method or a printing method in which patterning employing the shadow mask is not required. When the light emission layer only is formed by patterning, the layer formation method, although not specifically limited, is carried out preferably according to a deposition method, an ink jet method or a printing method. When a deposition method is used as the layer formation method, patterning of the layer is preferably carried out employing a shadow mask.

Further, the organic EL device can be prepared in the reverse order, in which the cathode, the electron injecting layer, the electron transporting layer, the light emission layer, the hole transporting layer, the hole injecting layer, and the anode are formed in that order. When a direct current voltage, a voltage of 2 to 40 V is applied to the thus obtained multicolor display, setting the anode as a + polarity and the cathode as a − polarity, light emission occurs. When voltage is applied with the reverse polarity, no current flows, and light is not emitted at all. When an alternating voltage is applied, light emission occurs only at the time when the polarity of the anode is "+" and that of the cathode is "−". The wave shape of the alternating current may be any one.

The multicolor display of the invention can be used as a display device, a display, or various light emission sources. The display device or the display, which employs three kinds of organic EL devices, a device emitting a blue light, a device emitting a red light and a device emitting a green light, can present a full color image.

Examples of the display device or the display include a television, a personal computer, a mobile device or an AV device, a display for text broadcasting, and an information display used in a car. The multicolor emission apparatus may be used as particularly a display for reproducing a still image or a moving image. When the apparatus is used as a display for reproducing a moving image, the driving method may be either a simple matrix (passive matrix) method or an active matrix method.

Examples of the illuminating device of the invention include a home lamp, a room lamp in a car, a backlight for a watch or a liquid crystal, a light source for boarding advertisement, a signal device, a light source for a photo memory medium, a light source for an electrophotographic copier, a light source for an optical communication instrument, and a light source for an optical sensor, but are not limited thereto.

The organic EL device of the invention may be an organic EL device having a resonator structure. The organic EL device having a resonator structure is applied to a light source for a photo-memory medium, a light source for an electrophotographic copier, a light source for an optical communication instrument, or a light source for a photo-sensor, but its application is not limited thereto. In the above application, a laser oscillation may be carried out.

<<Display>>

The organic EL device of the invention can be used as a lamp such as an illuminating lamp or a light source for exposure, as a projection device for projecting an image, or as a display for directly viewing a still image or a moving image. When the device is used in a display for reproducing a moving image, the driving method may be either a simple matrix (passive matrix) method or an active matrix method. The display can present a full color image, employing two or more kinds of organic EL devices each emitting light with a different color. A monochromatic color, for example, a white color can be converted to a full color of BGR, employing a color filter. Further, employing a color conversion filter, light color emitted from the organic EL device can be converted to another color or full color, where the λmax of the light emitted from the organic EL device is preferably not more than 480 nm.

One example of the display comprising the organic EL device of the invention will be explained below employing Figures.

FIG. 1 is a schematic drawing of one example of a display comprising an organic EL device. FIG. 1 is a display such as that of a cellular phone, displaying image information due to light emission from the organic EL.

A display 1 comprises a display section A having plural pixels and a control section B carrying out image scanning based on image information to display an image in the display section A.

The control section B is electrically connected to the display section A, transmits a scanning signal and an image data signal to each of the plural pixels based on image information from the exterior, and conducts image scanning which emits light from each pixel due to the scanning signal according to the image data signal, whereby an image is displayed on the display section A.

Figure 2:
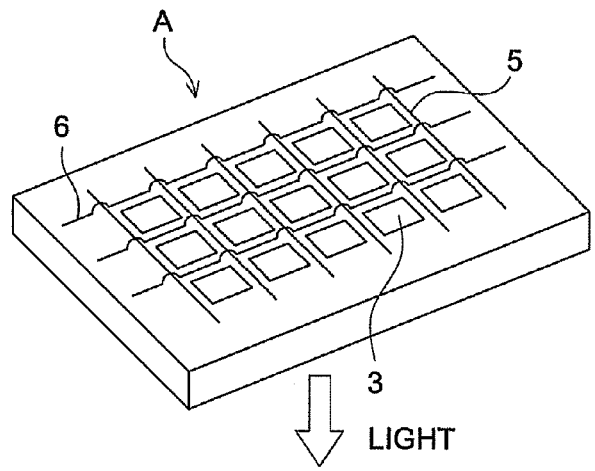
FIG. 2 is a schematic drawing of display section A.

FIG. 2 is a schematic drawing of a display section A.

The display section A comprises a glass substrate, plural pixels 3, and a wiring section comprising plural scanning lines 5 and plural data lines 6. The main members of the display section A will be explained below. In FIG. 2, light from pixels 3 is emitted in the direction of an arrow.

The plural scanning lines 5 and plural data lines 6 of the wiring section each are composed of an electroconductive material, the lines 5 and the lines 6 being crossed with each other at a right angle, and connected with the pixels 3 at the crossed points (not illustrated).

The plural pixels 3, when the scanning signal is applied from the scanning lines 5, receive the data signal from the data lines 6, and emit light corresponding to the image data received. Provision of red light emission pixels, green light emission pixels, and blue light emission pixels side by side on the same substrate can display a full color image.

Next, an emission process of pixels will be explained.

Figure 3:
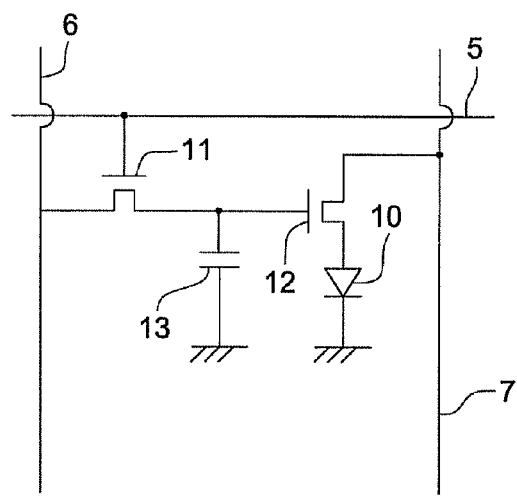
FIG. 3 is an equivalent circuit drawing of a driving circuit constituting a pixel.

FIG. 3 is a schematic drawing of a pixel.

The pixel comprises an organic EL device 10, a switching transistor 11, a driving transistor 12, and a capacitor 13. When a pixel with a red light emission organic EL device, a pixel with a green light emission organic EL device, and a pixel with a blue light emission organic EL device are provided side by side on the same substrate, a full color image can be displayed.

In FIG. 3, an image data signal is applied through the data lines 6 from the control section B to a drain of the switching transistor 11, and when a scanning signal is applied to a gate of the switching transistor 11 through the scanning lines 5 from the control section B, the switching transistor 11 is switched on, and the image signal data applied to the drain is transmitted to the capacitor 13 and the gate of the driving transistor 12.

The capacitor 13 is charged according to the electric potential of the image data signal transmitted, and the driving transistor 12 is switched on. In the driving transistor 12, the drain is connected to an electric source line 7, and the source to an organic EL device 10. Current is supplied from the electric source line 7 to the organic EL device 10 according to the electric potential of the image data signal applied to the gate.

The scanning signal is transmitted to the next scanning line 5 according to the successive scanning of the control section B, the switching transistor 11 is switched off. Even if the switching transistor 11 is switched off, the driving transistor 12 is turned on since the capacitor 13 maintains a charged potential of image data signal, and light emission from the organic EL device 10 continues until the next scanning signal is applied. When the next scanning signal is applied according the successive scanning, the driving transistor 12 works according to an electric potential of the next image data signal synchronized with the scanning signal, and light is emitted from the organic EL device 10.

That is, light is emitted from the organic EL device 10 in each of the plural pixels 3 due to the switching transistor 11 as an active device and the driving transistor 12 each being provided in the organic EL device 10 of each of the plural pixels 3. This emission process is called an active matrix process. Herein, light emission from the organic EL device 10 may be emission with plural gradations according to image signal data of multiple value having plural gradation potentials, and emission due to on-off according to a binary value of the image data signals.

The electric potential of the capacitor 13 may maintain till the next application of the scanning signal, or may be discharged immediately before the next scanning signal is applied.

In the invention, light emission may be carried out employing a passive matrix method as well as the active matrix method as described above. The passive matrix method is one in which light is emitted from the organic EL device according to the data signal only when the scanning signals are scanned.

FIG. 4 is a schematic drawing of a display employing a passive matrix method. In FIG. 4, pixels 3 are provided between the scanning lines 5 and the data lines 6 crossing with each other.

When scanning signal is applied to scanning line 5 according to successive scanning, pixel 3 connecting the scanning line 5 emits according to the image data signal. The passive matrix method has no active device in the pixel 3, which reduces manufacturing cost of a display.

The organic EL materials in the invention are applied to an organic EL device emitting a substantially white light as an illuminating device. Plural color lights emit from plural light emitting materials and are mixed to obtain a white light. As such an admixture of the plural color lights, there is an admixture of the emission maximum wavelength of each of three primary colors blue, green and red or an admixture of the emission maximum wavelength of each of complementary colors such as blue and yellow or blue-green and orange.

As a combination of light emitting materials to obtain plural emission colors, there is a combination of plural light emitting materials (emitting dopants) emitting plural phosphorescence or fluorescence or a combination of materials emitting phosphorescence or fluorescence and dyes, which are excited by light from the light emitting materials to emit light. In the white light emitting organic EL device regarding the invention, a combination of plural emitting dopants is preferred.

As a layer structure of the organic EL device to obtain plural emission colors, there is mentioned a single light emission layer containing plural emission dopants, plural light emission layers each containing a emission dopant having a different emission wavelength, a layer in which pixels emitting light with a different wavelength are formed in a matrix form.

In the white light-emitting organic EL device, patterning may be carried out through a metal mask or according to an ink-jet printing method. The patterning may be carried out only in electrodes, in both electrodes and light emission layer, or in all the layers of the organic EL device.

The light emitting materials used in the light emission layer are not specifically limited. For example, in a back light of a liquid crystal display, platinum complex in the invention or known light emitting materials are appropriately selected to suit the wavelength range corresponding to the CF (color filter) and mixed to obtain a white light.

The white light-emitting organic EL device can be applied to various light emission sources, an illuminating device such as a home lamp or a room lamp in a car, a lamp such as an exposure lamp and a backlight for a liquid crystal display, besides the displaying device as described above or a display.

Further, the white light-emitting organic EL device can be applied to a backlight for a watch, a light source for boarding advertisement, a signal device, a light source for a photo memory medium, a light source for an electrophotographic copier, a light source for an optical communication instrument, and a light source for an optical sensor or home electric appliances requiring a displaying device.

EXAMPLES

The present invention will be explained in the following examples, but is not limited thereto.

Example 1

<Preparation of Organic EL Element samples 1-1 Through 1-20>

A pattern was formed on a substrate (NA45, manufactured by NH Technoglass Co., Ltd.) composed of a glass plate (100 mm×100 mm×1.1 mm) and a 100 nm ITO (indium tin oxide) layer as an anode. Then the resulting transparent substrate having the ITO transparent electrode was subjected to ultrasonic washing in isopropyl alcohol, dried by a dry nitrogen gas and subjected to UV-ozone cleaning for 5 minutes. The thus obtained transparent substrate was fixed on a substrate holder of a vacuum deposition apparatus available on the market. Further, 200 mg of α-NPD were put in a first resistive heating molybdenum boat, 200 mg of CBP as a host compound were put in a second resistive heating molybdenum boat, 200 mg of bathocuproine (BCP) were put in a third resistive heating molybdenum boat, 100 mg of Ir-12 were put in a fourth resistive heating molybdenum boat, and 200 mg of Alq$_3$ were put in a fifth resistive heating molybdenum boat. The resulting boats were placed in the vacuum deposition apparatus.

Subsequently, pressure in the vacuum tank was reduced to 4×10$^{-4}$ Pa. Then, the boat carrying α-NPD being heated by supplying an electric current to the boat, α-NPD was deposited onto the transparent substrate at a depositing speed of 0.1 nm/sec to form a hole transporting layer. After that, the boat carrying CBP and the boat carrying Ir-12 being heated by supplying an electric current to both boats, CBP at a depositing speed of 0.2 nm/sec and Ir-12 at a depositing speed of 0.012 nm/sec were co-deposited onto the resulting hole transporting layer to form a light emission layer. The temperature of the substrate at the time of the deposition was room temperature. Subsequently, the boat carrying BCP being heated by supplying an electric current to the boat, BCP was deposited onto the resulting light emission layer at a depositing speed of 0.1 nm/sec to form a hole inhibiting layer with a thickness of 10 nm. Further, the boat carrying Alq$_3$ being heated by supplying an electric current to the boat, Alq$_3$ was deposited onto the resulting hole inhibiting layer at a depositing speed of 0.1 nm/sec to form an electron transporting layer with a thickness of 40 nm. The temperature of the substrate at the time of the deposition was room temperature.

After that, a 0.5 nm thick lithium fluoride layer and a nm thick aluminum layer were deposited on the resulting material to form a cathode. Thus, organic EL device sample was prepared.

Organic EL device samples 1-2 through 1-20 were prepared in the same manner as organic EL device sample 1-1 above, except that compounds as shown in Table 1 were used in the light emission layer instead of the host compound CBP.

The chemical structures of compounds used in the above are shown below.

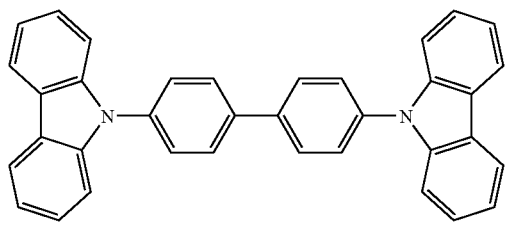

CBP

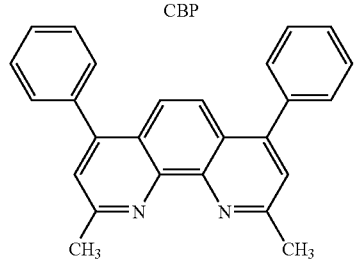

BCP

-continued

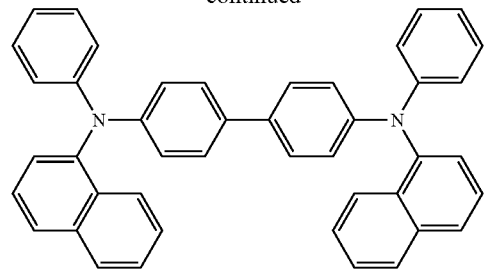

α-NPD

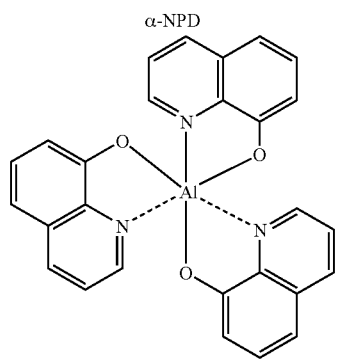

Alq$_3$

Comparative compound (1)

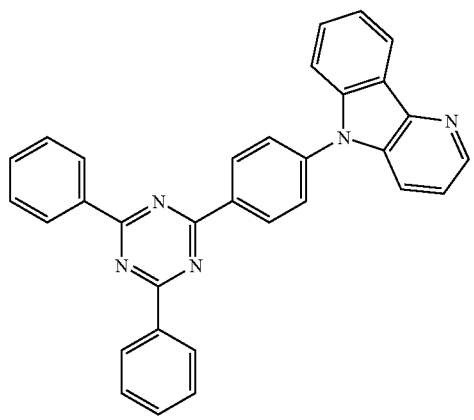

<<Evaluation of Organic EL Device Samples 1-1 Through 1-20>>

The organic EL device samples 1-1 through 1-20 obtained above were evaluated according to the following method.

(Luminance)

Luminance (cd/m$^2$) was measured employing a spectral radiance meter CS-1000 (produced by Konica Minolta Sensing Co., Ltd.).

(External Quantum Efficiency)

Electric current of 2.5 mA/cm$^2$ was supplied to each sample at 23° C. in an atmosphere of a dry nitrogen gas, external quantum efficiency (%) of each sample was measured. The external quantum efficiency (%) was measured employing a spectral radiance meter CS-1000 (produced by Konica Minolta Sensing Co., Ltd.).

Luminance and external quantum efficiency in the following Table were expressed by a relative value when luminance and external quantum efficiency of organic EL device sample 1-1 were set at 100, respectively. The results are shown in Table 1.

TABLE 1

| Organic EL device sample No. | Host compound | Luminance | External quantum efficiency | Remarks |
|---|---|---|---|---|
| 1-1 | CBP | 100 | 100 | Comp. |
| 1-2 | Comparative compound (1) | 89 | 79 | Comp. |
| 1-3 | 1-2 | 190 | 180 | Inv. |
| 1-4 | 1-4 | 178 | 185 | Inv. |
| 1-5 | 1-5 | 193 | 182 | Inv. |
| 1-6 | 1-7 | 190 | 190 | Inv. |
| 1-7 | 1-10 | 195 | 200 | Inv. |
| 1-8 | 1-11 | 200 | 199 | Inv. |
| 1-9 | 1-15 | 200 | 196 | Inv. |
| 1-10 | 1-17 | 200 | 196 | Inv. |
| 1-11 | 1-21 | 197 | 195 | Inv. |
| 1-12 | 1-23 | 197 | 195 | Inv. |
| 1-13 | 1-25 | 185 | 186 | Inv. |
| 1-14 | 3-1 | 202 | 202 | Inv. |
| 1-15 | 3-5 | 200 | 200 | Inv. |
| 1-16 | 3-7 | 185 | 181 | Inv. |
| 1-17 | 3-9 | 20 | 200 | Inv. |
| 1-18 | 3-12 | 198 | 198 | Inv. |
| 1-19 | 3-13 | 198 | 187 | Inv. |
| 1-20 | 3-15 | 195 | 197 | Inv. |

Comp.: Comparative, Inv.: Inventive

As is apparent from Table above, inventive organic EL device samples provide high luminance and excellent external quantum efficiency as compared to comparative organic EL device samples.

Example 2

<<Preparation of Organic EL Device Samples 2-1 Through 2-15>>

A pattern was formed on a substrate (NA45, manufactured by NH Technoglass Co., Ltd.) composed of a glass plate (100 mm×100 mm×1.1 mm) and a 100 nm ITO (indium tin oxide) layer as an anode. Then the resulting transparent substrate having the ITO transparent electrode was subjected to ultrasonic washing in isopropyl alcohol, dried by a dry nitrogen gas and subjected to UV-ozone cleaning for 5 minutes. The thus obtained transparent substrate was fixed on a substrate holder of a vacuum deposition apparatus available on the market. Further, 200 mg of α-NPD were put in a first resistive heating molybdenum boat, 200 mg of CBP were put in a second resistive heating molybdenum boat, 200 mg of BCP as a hole inhibiting material were put in a third resistive heating molybdenum boat, 100 mg of Ir-1 were put in a fourth resistive heating molybdenum boat, and 200 mg of $Alq_3$ were put in a fifth resistive heating molybdenum boat. The resulting boats were placed in the vacuum deposition apparatus.

Subsequently, pressure in the vacuum tank was reduced to $4 \times 10^{-4}$ Pa. Then the boat carrying α-NPD being heated by supplying an electric current to the boat, α-NPD was deposited onto the transparent substrate at a depositing speed of 0.1 nm/sec to form a hole transporting layer. After that, the boat carrying CBP and the boat carrying Ir-1 being heated by supplying an electric current to both boats, CBP at a depositing speed of 0.2 nm/sec and Ir-1 at a depositing speed of 0.012 nm/sec were co-deposited onto the resulting hole transporting layer to form a light emission layer. The temperature of the substrate at the time of the deposition was room temperature. Subsequently, the boat carrying BCP being heated by supplying an electric current to the boat, BCP was deposited onto the resulting light emission layer at a depositing speed of 0.1 nm/sec to form a hole inhibiting layer with a thickness of 10 nm. Further, the boat carrying $Alq_3$ being heated by supplying an electric current to the boat, $Alq_3$ was deposited onto the resulting hole inhibiting layer at a depositing speed of 0.1 nm/sec to form an electron transporting layer with a thickness of 40 nm. The temperature of the substrate at the time of the deposition was room temperature.

After that, a 0.5 nm thick lithium fluoride layer and a 110 nm thick aluminum layer were deposited on the resulting material to form a cathode. Thus, organic EL device sample 2-1 was prepared.

Organic EL device samples 2-2 through 2-15 were prepared in the same manner as organic EL device sample 2-1 above, except that compounds as shown in the following Table were used instead of the hole inhibiting material BCP.

<<Evaluation of Organic EL Device Samples 2-1 Through 2-15>>

The organic EL device samples 2-1 through 2-15 obtained above were evaluated for luminance and external quantum efficiency in the same manner as in Example 1. Further, lifetime was evaluated according to the following procedures.

(Lifetime)

When electric current of 2.5 mA/cm² was supplied to each sample, time required to reduce to half of luminance (initial luminance) at the beginning of emission was determined as a half-life period (τ0.5) and evaluated as a measure of lifetime. The Luminance was measured employing a spectral radiance meter CS-1000 (produced by Konica Minolta Sensing Co., Ltd.).

The results are shown in the following Table. Luminance, external quantum efficiency and lifetime in the following Table were expressed by a relative value when luminance, external quantum efficiency and lifetime of organic EL device sample 2-1 were set at 100, respectively.

TABLE 2

| Organic EL device sample No. | Hole inhibiting material | Luminance | External quantum efficiency | Lifetime | Remarks |
|---|---|---|---|---|---|
| 2-1 | BCP | 100 | 100 | 100 | Comp. |
| 2-2 | 1-1 | 113 | 112 | 284 | Comp. |
| 2-3 | 1-3 | 113 | 115 | 332 | Inv. |
| 2-4 | 1-5 | 114 | 113 | 521 | Inv. |
| 2-5 | 1-10 | 118 | 117 | 300 | Inv. |
| 2-6 | 1-12 | 119 | 118 | 550 | Inv. |
| 2-7 | 1-18 | 120 | 120 | 364 | Inv. |
| 2-8 | 1-22 | 118 | 118 | 300 | Inv. |
| 2-9 | 1-24 | 118 | 117 | 570 | Inv. |
| 2-10 | 3-1 | 124 | 122 | 440 | Inv. |
| 2-11 | 3-2 | 125 | 126 | 560 | Inv. |
| 2-12 | 3-8 | 113 | 111 | 620 | Inv. |
| 2-13 | 3-11 | 119 | 119 | 380 | Inv. |
| 2-14 | 3-14 | 114 | 114 | 270 | Inv. |
| 2-15 | 3-16 | 117 | 116 | 337 | Inv. |

Comp.: Comparative, Inv.: Inventive

As is apparent from Table above, inventive organic EL device samples provide high luminance, excellent external quantum efficiency and long lifetime as compared to comparative organic EL device samples.

Example 3

<<Evaluation of Organic EL Device Samples 3-1 Through 3-8>>

Organic EL device samples 3-1 through 3-8 were prepared in the same manner as organic EL device sample 1-1 of Example 1, except that compounds as shown in the following Table were used as a host compound, Ir-1 was used instead of Ir-12, and B-Alq was used instead of BCP.

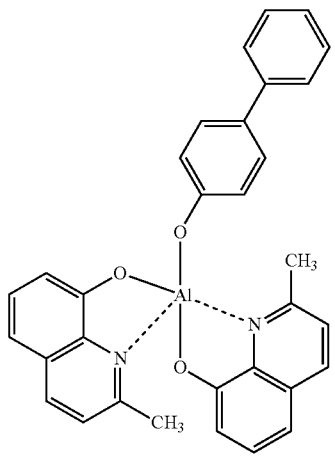

B-Alq

<<Evaluation of Organic EL Device Samples 3-1 Through 3-8>>

The organic EL device samples 3-1 through 3-8 obtained above were evaluated for storage stability according to the following procedures.
(Storage Stability)

Each of organic EL device samples 3-1 through 3-8 was allowed to store at 85° C. for 24 hours. Electric current of 2.5 mA/cm² being supplied to the sample before and after storage, luminance was measured. The luminance ratio of luminance of sample after storage to that of sample before storage was calculated according to the following formula, and evaluated as a measure of storage stability.

Storage stability (%)=Luminance (2.5 mA/cm²) of sample after storage/Luminance (2.5 mA/cm²) of sample before storage×100

The results are shown in the following Table.

TABLE 3

| Organic EL device sample No. | Host compound | Storage stability (%) | Remarks |
|---|---|---|---|
| 3-1 | CBP | 48 | Comparative |
| 3-2 | 1-1 | 64 | Inventive |
| 3-3 | 1-7 | 63 | Inventive |
| 3-4 | 1-11 | 79 | Inventive |
| 3-5 | 1-17 | 78 | Inventive |
| 3-6 | 3-1 | 83 | Inventive |
| 3-7 | 3-9 | 83 | Inventive |
| 3-8 | 3-15 | 76 | Inventive |

As is apparent from Table above, inventive organic EL device samples provide high storage stability as compared to the comparative organic EL device sample.

Example 4

<<Evaluation of Organic EL Device Samples 4-1 Through 4-8>>

Organic EL device samples 4-1 through 4-8 were prepared in the same manner as organic EL device sample 2-1 of Example 2, except that Exemplified compound 1-5 was used in the light emission layer instead of the host compound CBP, and the hole inhibiting compound in the hole inhibiting layer was changed to those as shown in Table 4.

<<Evaluation of Organic EL Device Samples 4-1 Through 4-8>>

The organic EL device samples 4-1 through 4-8 obtained above were evaluated for storage stability in the same manner as in Example 3. The results are shown in the following Table.

TABLE 4

| Organic EL device sample No. | Host compound | Storage stability (%) | Remarks |
|---|---|---|---|
| 4-1 | B-Alq | 67 | Comparative |
| 4-2 | 1-4 | 73 | Inventive |
| 4-3 | 1-10 | 80 | Inventive |
| 4-4 | 1-12 | 81 | Inventive |
| 4-5 | 1-18 | 80 | Inventive |
| 4-6 | 3-2 | 83 | Inventive |
| 4-7 | 3-11 | 81 | Inventive |
| 4-8 | 3-14 | 74 | Inventive |

As is apparent from Table above, inventive organic EL device samples provide high storage stability as compared to the comparative organic EL device sample.

Example 5

Inventive organic EL device sample 1-14 prepared in Example 1, inventive organic EL device sample 2-13 prepared in Example 2, and a red light emission organic EL device sample, which was prepared in the same manner as organic EL device sample 2-13 except that the phosphorescent compound was changed to IR-9 were provided side by side on the same substrate. Thus, a full color image display according to an active matrix method was obtained which had a structure as shown in FIG. 1. FIG. 2 is a schematic drawing of a display section A of the full color image display prepared above. The display section comprises a base plate, and provided thereon, plural pixels 3 (including blue light emission pixels, green light emission pixels, and red light emission pixels) and a wiring section including plural scanning lines 5 and plural data lines 6. The plural scanning lines 5 and plural data lines 6 each are composed of electroconductive material. The plural scanning lines 5 and plural data lines 6 were crossed with each other at a right angle, and connected with the pixels 3 at the crossed points (not illustrated in detail). Each of the plural pixels 3, which comprise an organic EL element corresponding to the respective color, a switching transistor as an active element, and a driving transistor, is driven according to an active matrix system. The plural pixels 3, when scanning signal is applied from the scanning lines 5, receives the image data signal from the data lines 6, and emits light corresponding to the image data received. A full color image can be displayed by a red light emission pixel, a green light emission pixel, and a blue light emission pixel, each suitably arranged on the base plate.

A full color clear moving image was obtained by driving the full color image display prepared above.

Example 6

<<Preparation of Illuminating Device>>

The non-emitting surface of each of the blue light emission, green light emission and red light emission organic EL device samples obtained above was covered with a glass plate to obtain an illuminating device. The illuminating device can be used as a thin, white light-emitting illuminating device with high emission efficiency and long emission lifetime.

Figure 5:
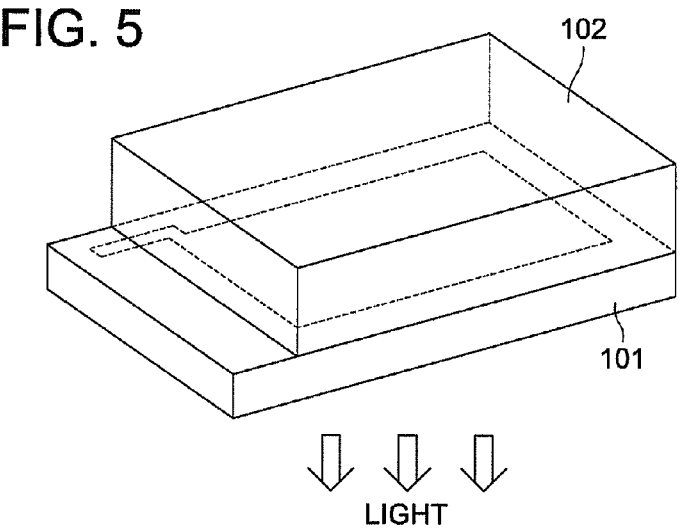
FIG. 5 is a schematic drawing of an illuminating device.
Figure 6:
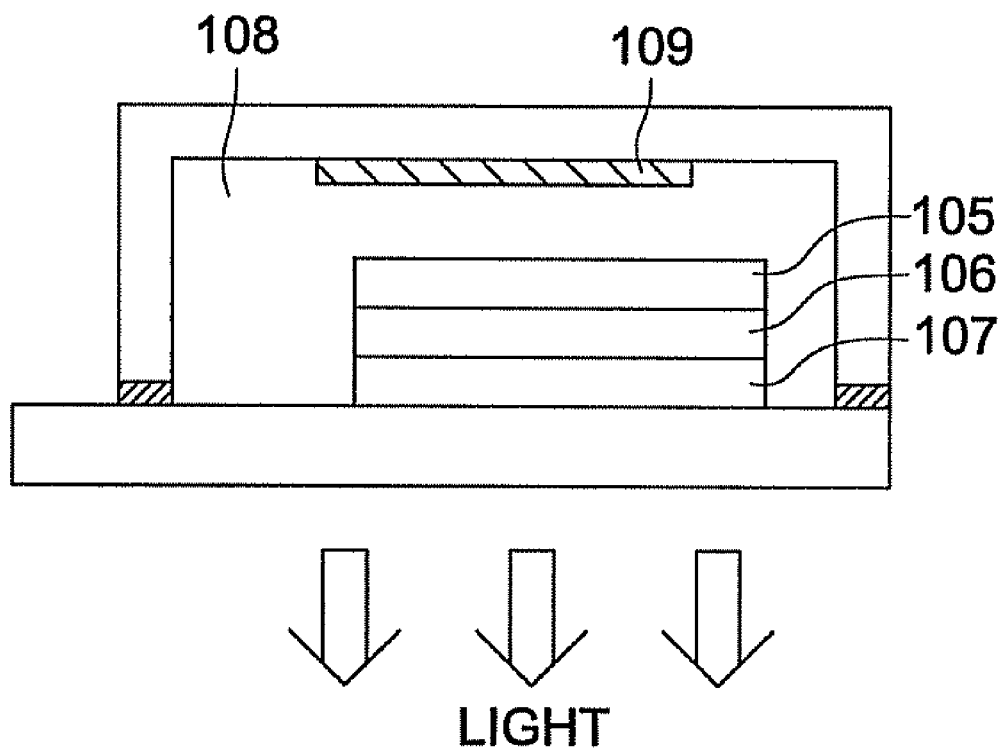
FIG. 6 is a sectional view of an illuminating device.

FIG. 5 is a schematic drawing of an illuminating device. FIG. 6 is a sectional view of an illuminating device. Organic EL device 101 is covered with a glass cover 102. Numerical No. 105 is a cathode, numerical No. 106 is an organic EL layer, and numerical No. 107 is a glass substrate with a transparent electrode. In the inside of the glass cover 102, nitrogen gas 108 is introduced and a water-trapping agent 109 is placed.

The invention claimed is:

1. An organic electroluminescent device comprising, between a pair of electrodes, a constituent layer including at least a phosphorescence emission layer comprising a metal complex containing a metal belonging to groups 8 through 10 of the periodic table as a center metal, wherein at least one in the constituent layer contains a compound represented by formula (1),

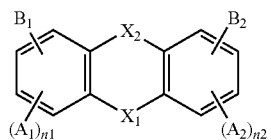

Formula (1)

wherein $A_1$ and $A_2$ represent a substituent; n1 and n2 independently represent an integer of from 0 to 3; $X_1$ represents an oxygen atom, a sulfur atom, an alkylene group, an imino group, a carbonyl group, a sulfoxide group or a sulfonyl group; $X_2$ represents an oxygen atom, a sulfur atom, an alkylene group, an imino group, a carbonyl group, a sulfoxide group, or a sulfonyl group provided that when $X_1$ represents an alkylene group, $X_2$ represents a sulfur atom, an imino group, a carbonyl group, a sulfoxide group, or a sulfonyl group; and $B_1$ and $B_2$ represent a group represented by formula (2),

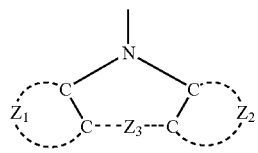

Formula (2)

wherein $Z_1$ and $Z_2$ represent an atomic group necessary to form a substituted or unsubstituted aromatic heterocyclic ring or a substituted or unsubstituted aromatic hydrocarbon ring; and $Z_3$ represents a divalent linkage group or a chemical bond.

2. The organic electroluminescent device of claim 1, wherein in formula (1), $X_1$ and $X_2$ independently represent an oxygen atom, a sulfur atom, an alkyene group, an imino group, a carbonyl group, a sulfoxide group or a sulfonyl group.

3. The organic electroluminescent device of claim 1, wherein $Z_1$ of formula (2) represents an atomic group necessary to form a substituted or unsubstituted aromatic hydrocarbon ring.

4. The organic electroluminescent device of claim 1, wherein the compound represented by formula (1) is contained in the phosphorescence emission layer.

5. The organic electroluminescent device of claim 1, wherein the constituent layer further includes at least one hole inhibiting layer containing the compound represented by formula (1).

6. The organic electroluminescent device of claim 1, emitting a blue light.

7. The organic electroluminescent device of claim 1, emitting a white light.

8. An organic electroluminescent device comprising, between a pair of electrodes, a constituent layer including at least a phosphorescence emission layer comprising a metal complex containing a metal belonging to groups 8 through 10 of the periodic table as a center metal, wherein at least one in the constituent layer contains a compound represented by formula (4),

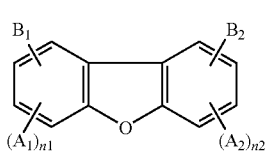

Formula (4)

wherein $A_1$ and $A_2$ represent a substituent; n1 and n2 independently represent an integer of from 0 to 3; and $B_1$ and $B_2$ represent a group represented by formula (2),

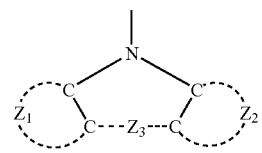

Formula (2)

wherein $Z_1$ and $Z_2$ represent an atomic group necessary to form a substituted or unsubstituted aromatic heterocyclic ring or a substituted or unsubstituted aromatic hydrocarbon ring; and $Z_3$ represents a divalent linkage group or a chemical bond.

9. The organic electroluminescent device of claim 8, wherein $Z_1$ of formula (2) represents an atomic group necessary to form a substituted or unsubstituted aromatic hydrocarbon ring.

10. The organic electroluminescent device of claim 8, wherein $Z_1$ of formula (2) represents an atomic group necessary to form a substituted or unsubstituted aromatic heterocyclic ring.

11. The organic electroluminescent device of claim 8, wherein the compound represented by formula (4) is contained in the phosphorescence emission layer.

12. The organic electroluminescent device of claim 8, wherein the constituent layer further includes at least one hole inhibiting layer containing the compound represented by formula (4).

13. The organic electroluminescent device of claim 8, emitting a blue light.

14. The organic electroluminescent device of claim 8, emitting a white light.

15. An organic electroluminescent device comprising, between a pair of electrodes, a constituent layer including at least a phosphorescence emission layer comprising a emetal complex containing a metal belonging to groups 8 to 10 of the periodic table as a center metal, wherein at least one in the constituent layer contains a compound represented by formula (1),

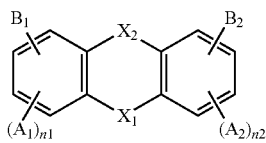

Formula (1)

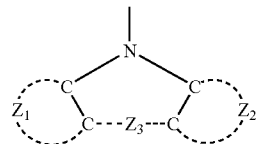

Formula (2)

wherein $A_1$ and $A_2$ represent a substituent; n1 and n2 independently represent an integer of from 0 to 3; $X_1$ represents an oxygen atom, a sulfur atom, an alkylene group, an imino group, a carbonyl group, a sulfoxide group or a sulfonyl group; $X_2$ represents an oxygen atom, a sulfur atom, an alkylene group, an imino group, a carbonyl group, a sulfoxide group, a sulfonyl group or a chemical bond provided that when $X_1$ represents an alklylene group, $X_2$ represents the sulfur atom, the imino group, the carbonyl group, the sulfoxide group the sulfonyl group or the chemical bond, and when $X_2$ represents the chemical bond, $X_1$ represents the imino group, the carbonyl group, the sulfoxide group or the sulfonyl group; and $B_1$ and $B_2$ represent a group represented by formula (2), wherein $Z_1$ represents an atomic group necessary to form a substituted or unsubstituted aromatic heterocyclic ring; $Z_2$ represents an atomic group necessary to form a substituted or unsubstituted aromatic heterocyclic ring or a substituted or unsubstituted aromatic hydrocarbon ring; and $Z_3$ represents a divalent linkage group or a chemical bond.

16. The organic electroluminescent device of claim 15, wherein in formula (1), X1 represents an oxygen atom, a sulfur atom, or a sulfonyl group.

\* \* \* \* \*